United States Patent
Liu et al.

(10) Patent No.: US 11,078,232 B2
(45) Date of Patent: Aug. 3, 2021

(54) PREPARATION AND USE OF MOLECULAR SITE TARGETED AND ACTIVATED KINASE INHIBITOR

(71) Applicant: Yafei Shanghai Biology Medicine Science & Technology Co. Ltd., Shanghai (CN)

(72) Inventors: Yuan Liu, Shanghai (CN); Cheng Liu, Shanghai (CN); Haiyang Wang, Shanghai (CN)

(73) Assignee: Yafei Shanghai Biology Medicine Science & Technology Co. Ltd., Shanghai (CN)

( * ) Notice: Subject to any disclaimer, the term of this patent is extended or adjusted under 35 U.S.C. 154(b) by 0 days.

(21) Appl. No.: 16/478,826

(22) PCT Filed: Jan. 16, 2018

(86) PCT No.: PCT/CN2018/072766
§ 371 (c)(1),
(2) Date: Jul. 17, 2019

(87) PCT Pub. No.: WO2018/133766
PCT Pub. Date: Jul. 26, 2018

(65) Prior Publication Data
US 2020/0140485 A1    May 7, 2020

(30) Foreign Application Priority Data

Jan. 17, 2017  (CN) .......................... 201710037230.9

(51) Int. Cl.
| | | |
|---|---|---|
| *C07K 5/08* | (2006.01) |
| *C07K 5/083* | (2006.01) |
| *A61K 47/65* | (2017.01) |
| *A61K 47/54* | (2017.01) |
| *A61P 35/00* | (2006.01) |
| *A61K 31/44* | (2006.01) |
| *C07D 213/81* | (2006.01) |
| *A61K 45/06* | (2006.01) |

(52) U.S. Cl.
CPC ............ *C07K 5/0806* (2013.01); *A61K 31/44* (2013.01); *A61K 47/54* (2017.08); *A61K 47/65* (2017.08); *A61P 35/00* (2018.01); *C07D 213/81* (2013.01); *C07K 5/081* (2013.01); *C07K 5/0808* (2013.01); *A61K 45/06* (2013.01)

(58) Field of Classification Search
CPC .... C07K 5/0806; C07K 5/0808; C07K 5/081; C07K 19/00; A61K 47/65; A61K 47/54; A61K 31/44; A61K 45/06; A61K 47/549; A61P 35/00; A61P 35/02; A61P 35/04; C07D 213/81
See application file for complete search history.

(56) References Cited

U.S. PATENT DOCUMENTS

2008/0019918 A1   1/2008  Aoki et al.

FOREIGN PATENT DOCUMENTS

| CN | 101259284 A | 9/2008 |
| CN | 105792850 A | 7/2016 |
| CN | 106344930 A | 1/2017 |
| WO | WO 2004/113274 A2 | 12/2004 |
| WO | WO 2016/026458 A1 | 2/2016 |

OTHER PUBLICATIONS

Pan et al, Carbohydrate Polymers, 2016, 812-820 (Year: 2016).*
International Search Report received in PCT/CN2018/072766 dated Apr. 12, 2018.
Office Action, dated Dec. 14, 2020, issued in Chinese Application No. 201710037230.9.

* cited by examiner

*Primary Examiner* — Sudhakar Katakam
(74) *Attorney, Agent, or Firm* — Knobbe, Martens, Olson & Bear LLP

(57) ABSTRACT

Disclosed are molecularly targeted and activated kinase inhibitors and use thereof. Specifically, a compound represented by the following formula A or a pharmaceutically acceptable salt thereof, wherein X is a polar and a non-polar uncharged amino acid such as alanine, proline or threonine; A is alanine; N is asparagine; PABC is —NH-phenyl-CH2-O—; and Z is a drug molecule; wherein the lactobionic acid residue, XAN and PABC are linked to each other by an amide bond; PABC is bonded to Z by an ester group, i.e., —OC(O)—.

6 Claims, 4 Drawing Sheets

Specification includes a Sequence Listing.

DOX    Succinyl-AANL-DOX    S3

PREPARATION AND USE OF MOLECULAR SITE TARGETED AND ACTIVATED KINASE INHIBITOR

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 2020-01-10 Sequence Listing—SHPT002.003APC, the date of creation of the ASCII text file is Jan. 10, 2020, and the size of the ASCII text file is 613 bytes.

TECHNICAL FIELD

The present invention relates to preparation and application of molecular site-directed and activated kinase inhibitors.

TECHNICAL BACKGROUND

The saccharide is a polyhydroxy (2 or more) aldehyde or ketone compound, which can become an organic compound of either of them after hydrolysis. Sugar molecules have different receptors on immune cells and tumor cells. For example, lactose (Lacto) has multiple receptors for action in human cells, including the sialoglycoprotein receptor. The interaction between sugar molecules and receptors serves as an inter-cell recognition and biomolecular recognition, and is involved in important applications such as cell communication.

Sorafenib is a new multi-targeted oral drug for the treatment of tumors with the following structure:

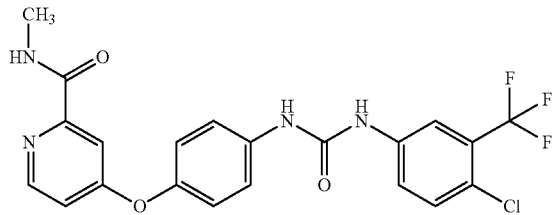 [SMILES: CNC(=O)c1cc(Oc2ccc(NC(=O)Nc3ccc(Cl)c(C(F)(F)F)c3)cc2)ccn1]

On Dec. 20, 2005, the US FDA quickly approved sorafenib as a first-line treatment for advanced renal cell carcinoma for the treatment of inoperable advanced renal cell carcinoma. Sorafenib can also be used to treat primary hepatocellular carcinoma that is inoperable or distantly metastatic, as well as to treat patients with locally recurrent or metastatic, progressively differentiated thyroids that are no longer effective for radioiodine therapy. In addition, the drug has a certain effect on non-small cell lung cancer as well as melanoma. Sorafenib is a small molecule targeted drug with dual anti-tumor effects. The main mechanisms of action are: 1) Sorafenib is a serine, threonine protein kinase (RAF) and tyrosine kinase inhibitor that inhibits RAF gene expression and inhibits RAF/MEK/ERK signaling pathways from directly inhibiting tumor growth. 2) Blocking tumor angiogenesis by inhibiting vascular endothelial growth factor receptor (VEGFR-1, VEGFR-2, VEGFR-3) and platelet-derived growth factor receptor beta (PDGFR-β), cutting the tumor cells nutritional supply to achieve the purpose of inhibiting tumor growth. However, sorafenib has serious adverse reactions, including rash, diarrhea, elevated blood pressure, redness, pain, swelling or blisters in the palms or feet, long-term use of lymphocytes declines, it is not suitable for patients with underlying liver disease and inhibits human immunity.

SUMMARY OF INVENTION

The present disclosure provides a compound having the following structure or a pharmaceutically acceptable salt thereof:

Lacto-XAN-PABC-Z         (Formula A)

wherein,

X is a polar and a non-polar uncharged amino acid such as alanine, proline or threonine;

A is alanine; N is asparagine;

PABC is —NH-phenyl-CH2-O—;

Z is a drug molecule;

In one or more embodiments of the present disclosure, the lactobionic acid residue linked to X via an amide bond (—C(O)—NH—).

In one or more embodiments of the present disclosure, X linked to A via an amide bond.

In one or more embodiments of the present disclosure, PABC linked to N via an amide bond.

In one or more embodiments of the present disclosure, PABC linked to Z via an ester bond (—O—C(O)—).

In one or more embodiments, Z is selected from the group consisting of doxorubicin, darafenib, dovetinib, motesanib, and the sorafenib derivative of Formula B.

In one or more embodiments, the compound of Formula A has the structure of Formula I below:

Formula I

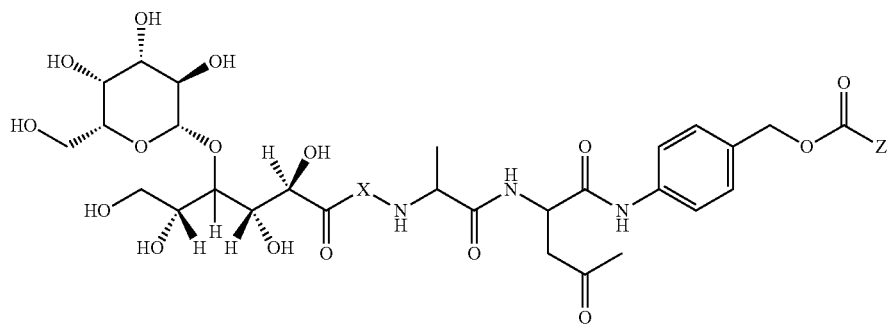

Wherein X and Z are as defined above.

In one or more embodiments, X is alanine, and the compound of Formula I has the structure of Formula II:
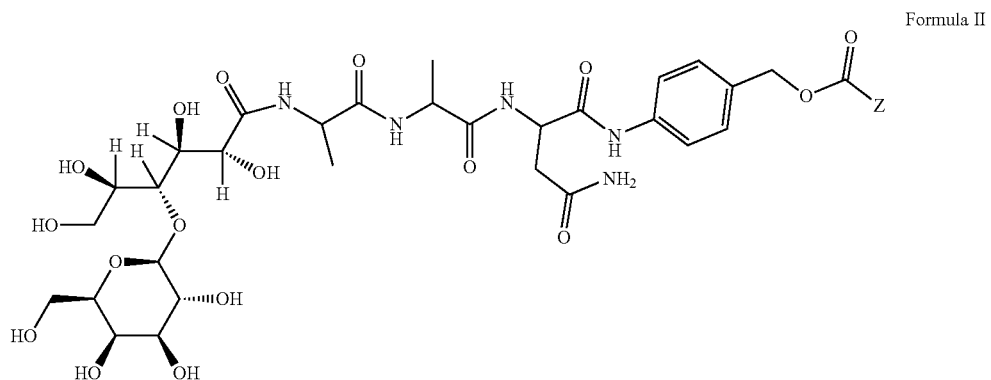
Formula II
In a particular embodiment, the compound of formula II is selected from the group consisting of:
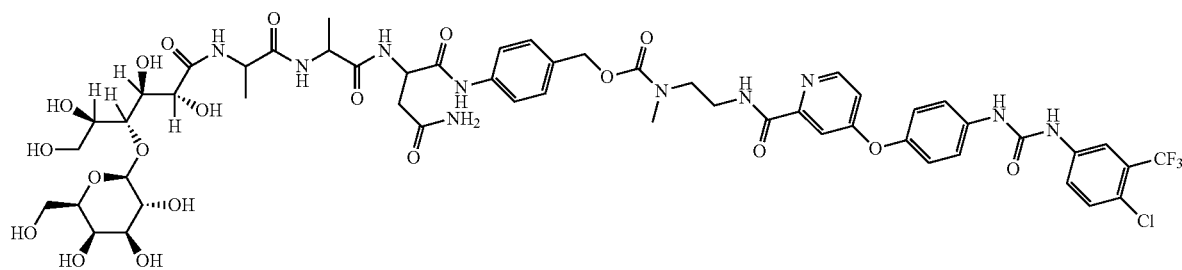
Lacto-AAN-PABC-Compound a
S1
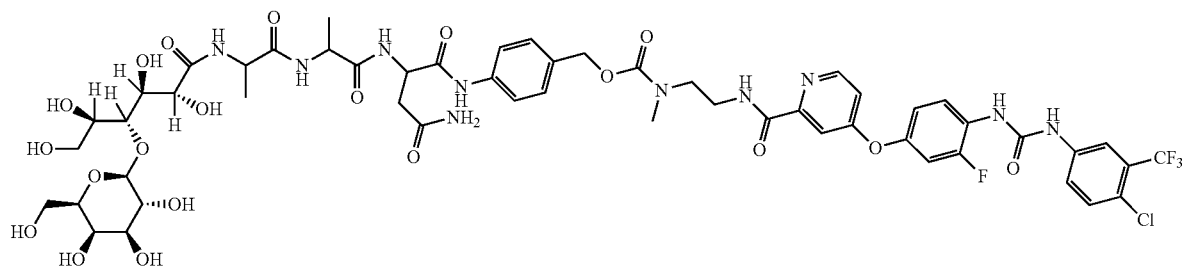
Lacto-AAN-PABC-Compound b
S2
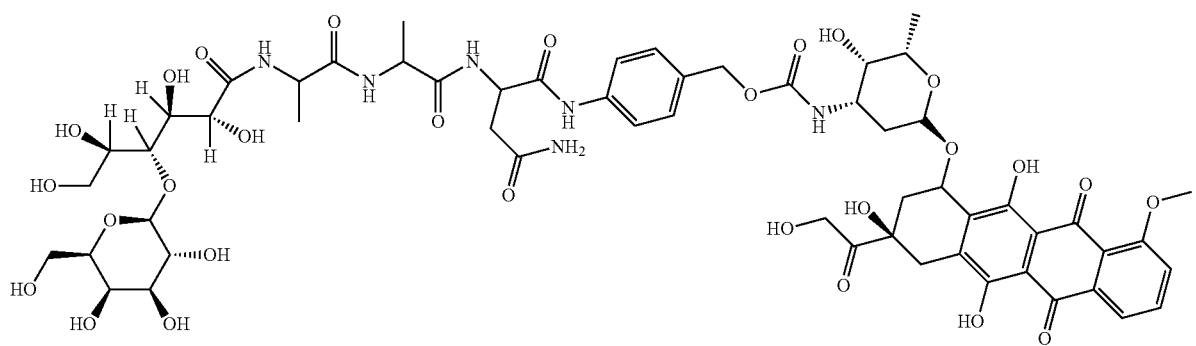
Lacto-AAN-PABC-Adriamycin
S3

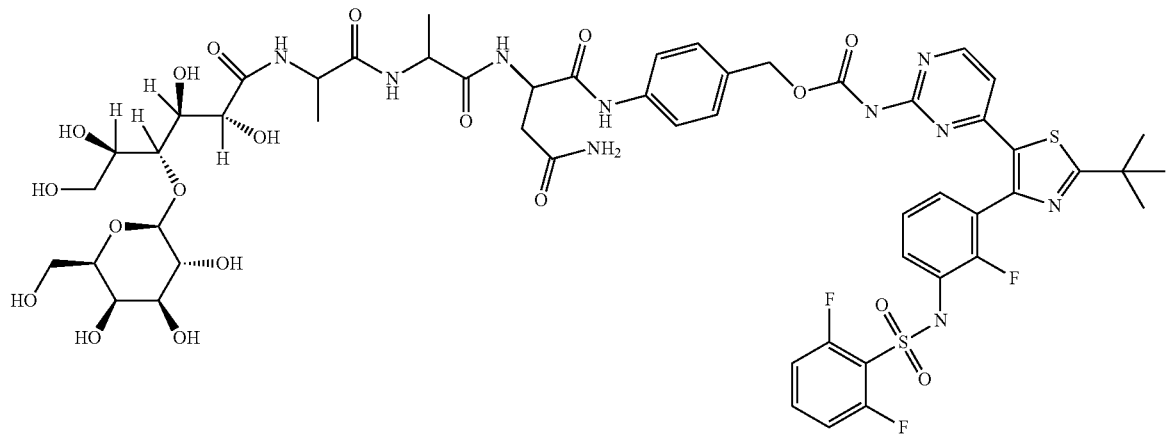
Lacto-AAN-PABC-Darafinib
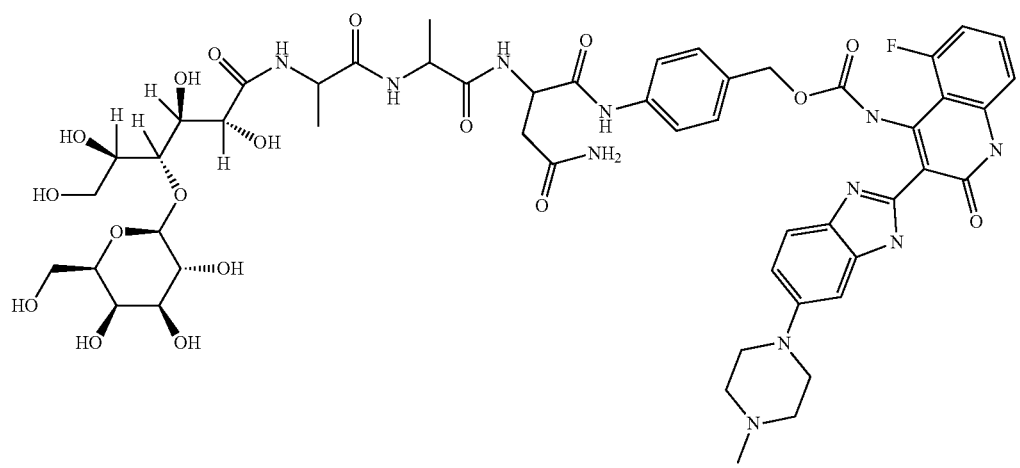
Lacto-AAN-PABC-Dovetinib
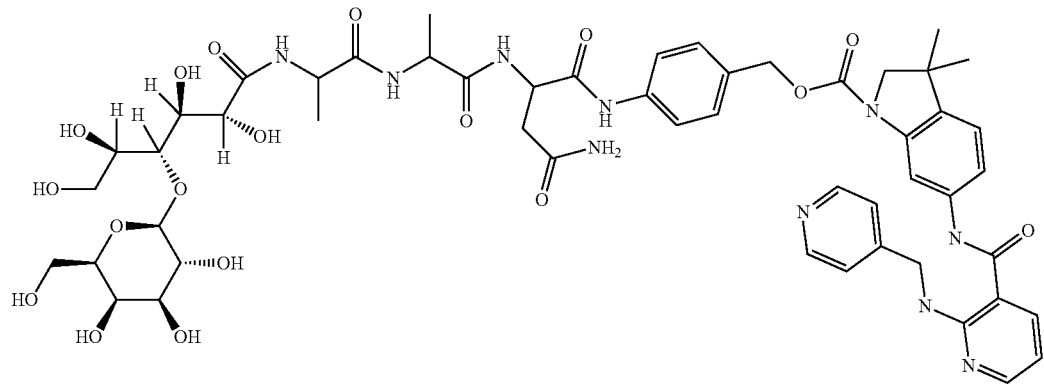
Lacto-AAN-PABC-Motesanib In a particular embodiment, X is valine, and the compound of formula I has the structure of formula III:
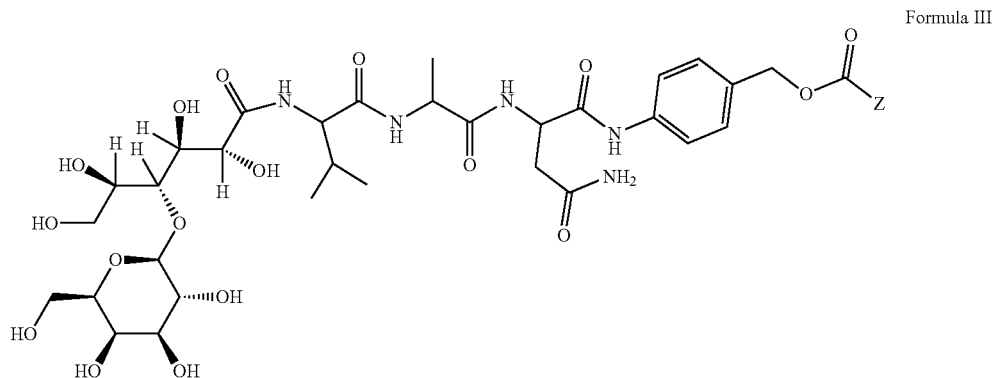
Formula III
In a specific embodiment, the compound of formula III is selected from the group consisting of:
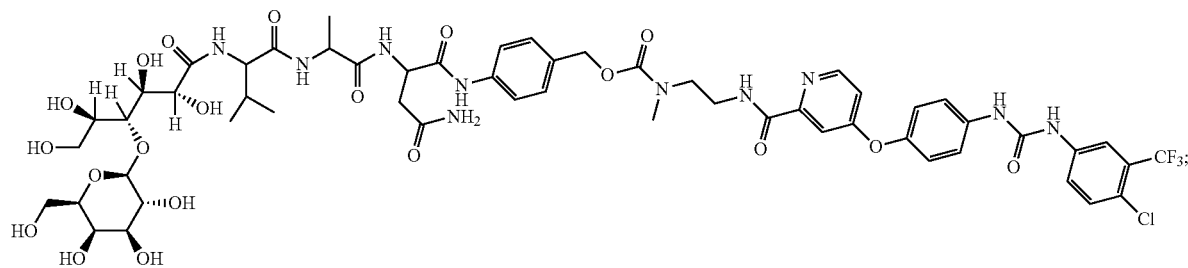
Lacto-VAN-PABC-Compound a
S7
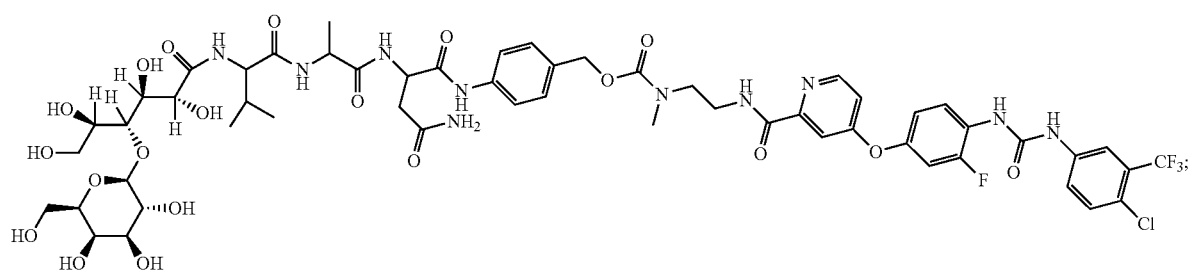
Lacto-VAN-PABC-Compound b
S8
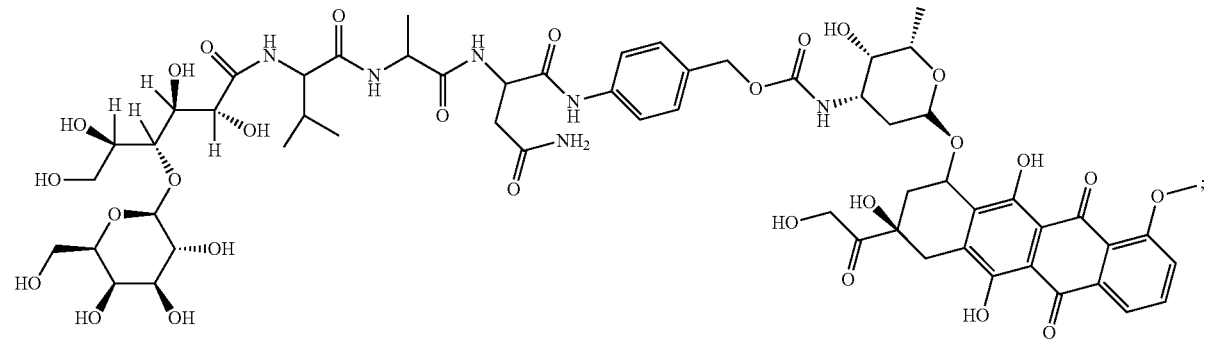
Lacto-VAN-PABC-Adriamycin
S9

-continued
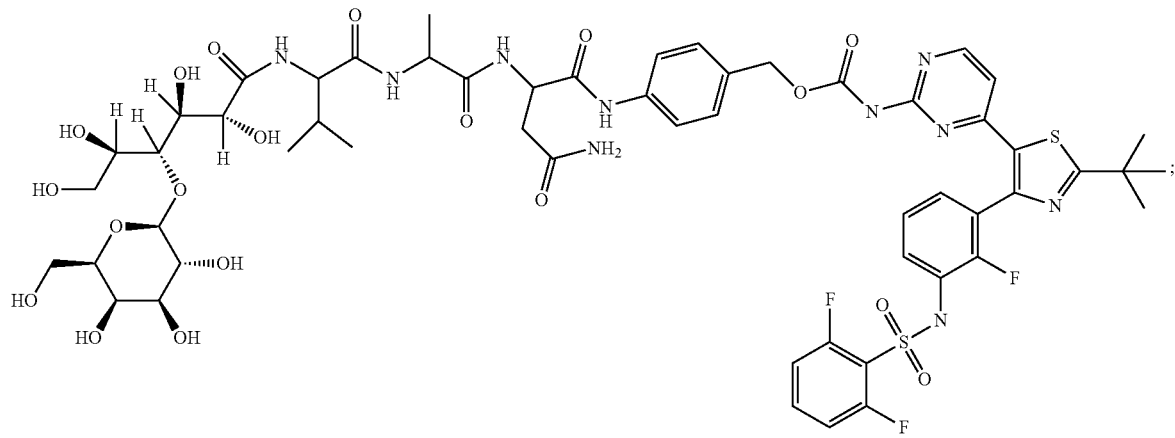
Lacto-VAN-PABC-Darafinib
S10
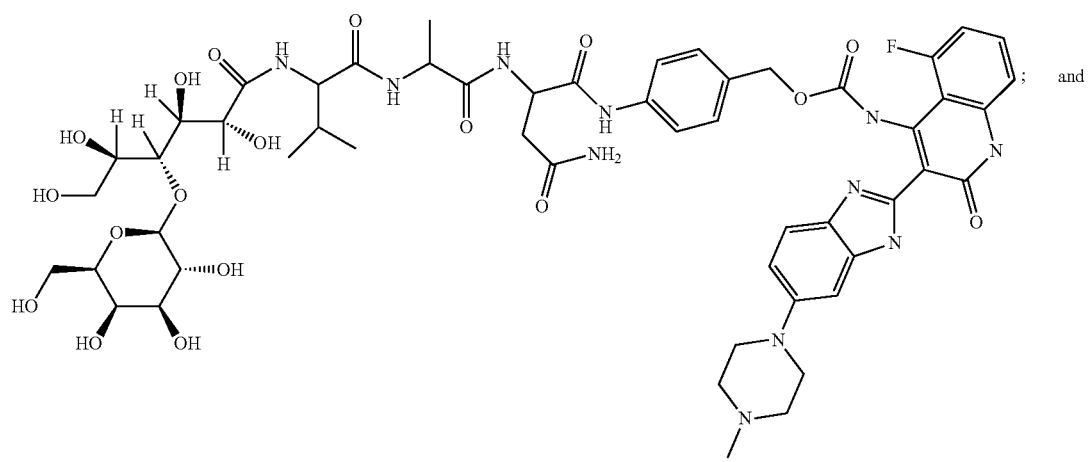
Lacto-AAN-PABC-Dovetinib
S11
and
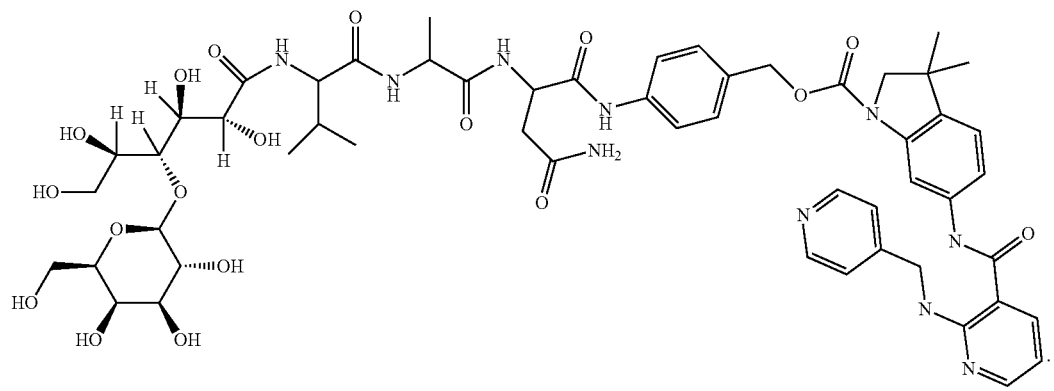
Lacto-VAN-PABC-Motesanib
S12

In a particular embodiment, X is threonine and the compound of formula I has the structure of formula IV:
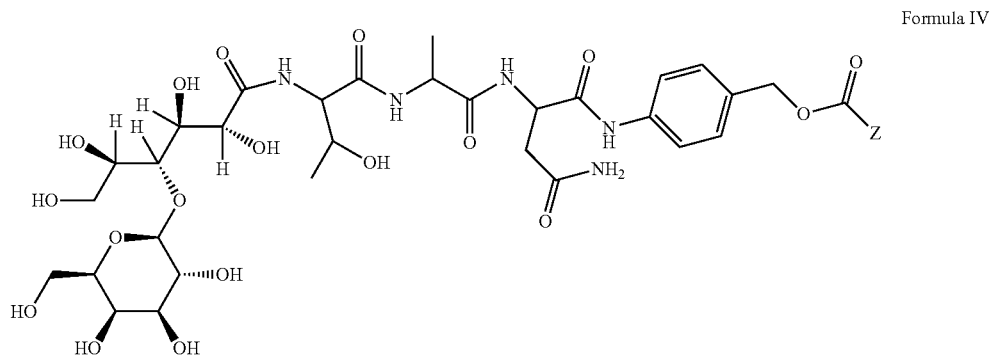
Formula IV
In a specific embodiment, the compound of formula IV is selected from the group consisting of:
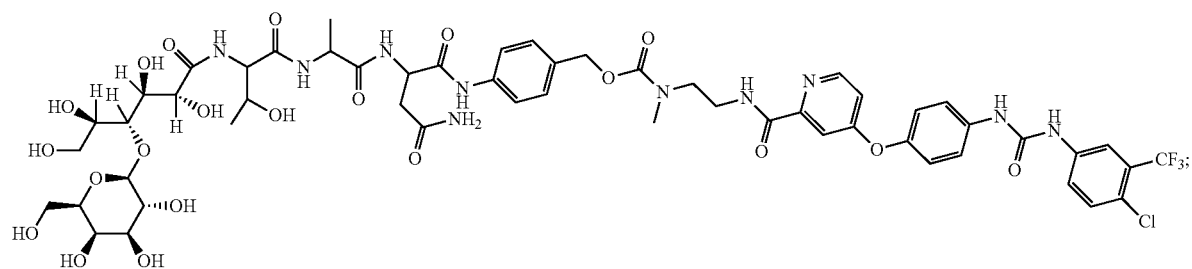
Lacto-TAN-PABC-Compound a
S13
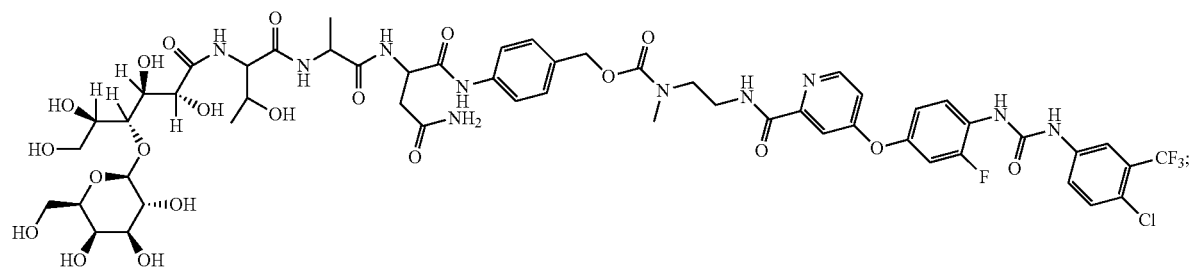
Lacto-TAN-PABC-Compound b
S14
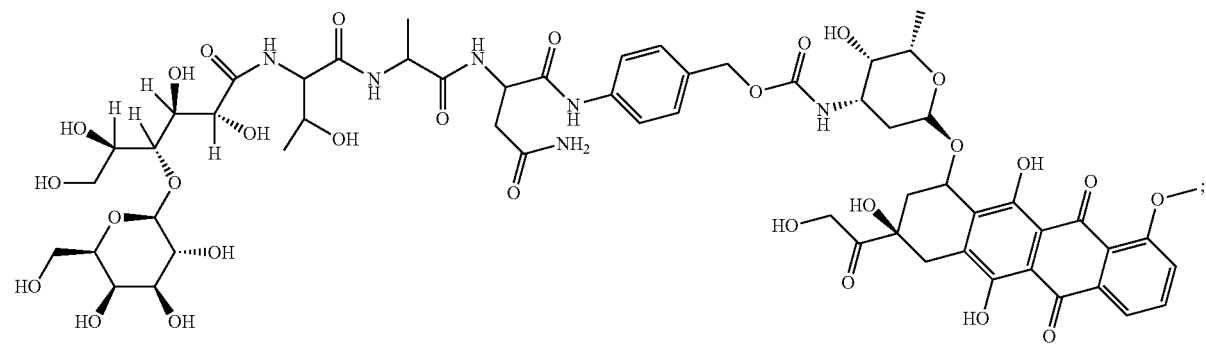
Lacto-TAN-PABC-Adriamycin
S15

-continued

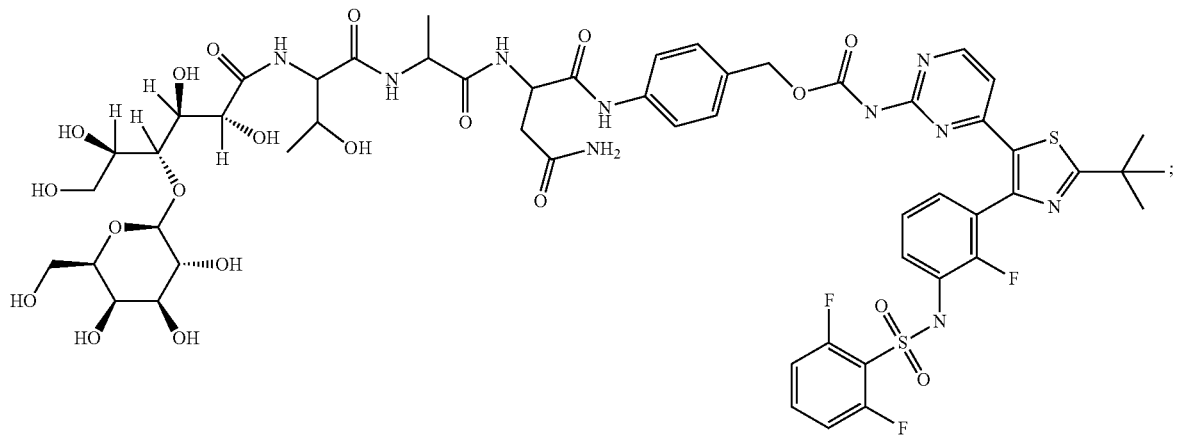
Lacto-TAN-PABC-Darafinib

S16

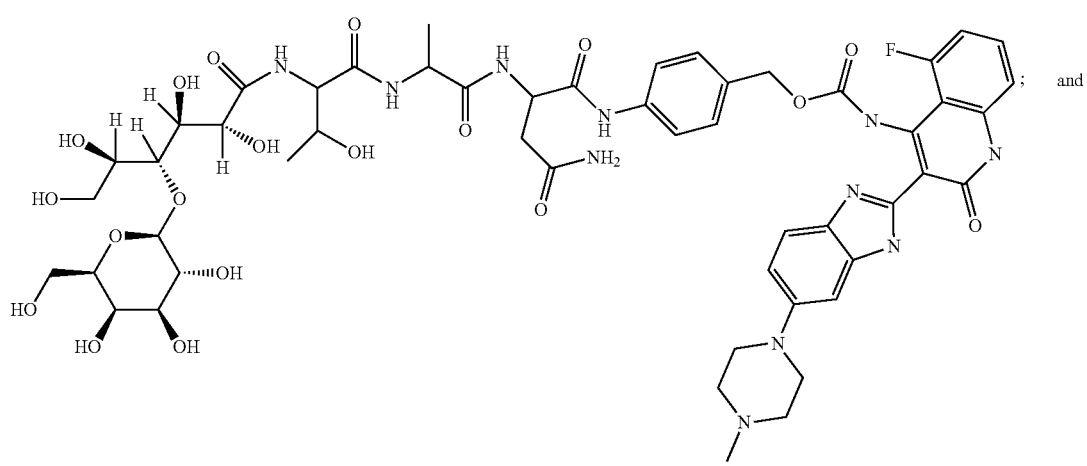
Lacto-TAN-PABC-Dovetinib

S17 ; and

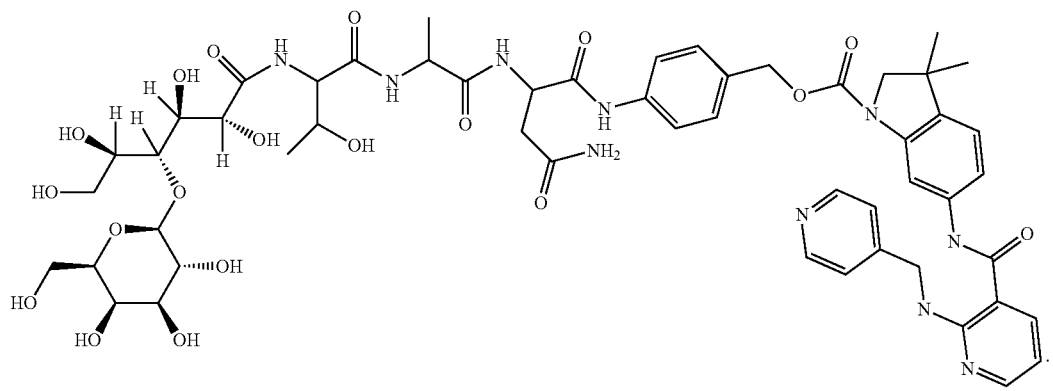
Lacto-TAN-PABC-Motesanib

S18

The present disclosure also provides a pharmaceutical composition comprising a compound of formula A as disclosed herein, or a pharmaceutically acceptable salt thereof, and a pharmaceutically acceptable carrier.

In one or more embodiments, the pharmaceutical composition comprises a compound of Formula I or a pharmaceutically acceptable salt thereof.

In one or more embodiments, the pharmaceutical composition contains any one or more of the compounds S1-S18 disclosed herein or a pharmaceutically acceptable salt thereof.

The present disclosure also provides the use of the compound of formula A or a pharmaceutically acceptable salt thereof for the manufacture of a medicament for the treatment of cancer or cancer cell metastasis.

In one or more embodiments, the cancer is selected from the group consisting of liver cancer, kidney cancer, thyroid cancer, colorectal cancer, bladder cancer, brain cancer, breast cancer, cervical cancer, rectal cancer, esophageal cancer, lung cancer (e g. bronchial lung cancer), including undifferentiated small cell and non-small cell), nasopharyngeal carcinoma, pancreatic cancer, prostate cancer, skin cancer, stomach cancer, uterine cancer, ovarian cancer, testicular cancer, blood cancer (such as chronic or acute leukemia, including lymphocytic And granulocyte leukemia), malignant lymphoma, cellulosic sarcoma, soft tissue sarcoma, osteosarcoma, rhabdomyosarcoma, Ewing's sarcoma, nephroblastoma, neuroblastoma, thyroid cancer, and head and neck squamous cell carcinoma.

The present disclosure also provides the use of the compound of formula A or a pharmaceutically acceptable salt thereof for the preparation of an immunotherapeutic agent.

In one or more embodiments, the immunotherapeutic agent can be used to stimulate T cell proliferation and invasion of a lesion, inhibit tumor-associated macrophages, and/or promote a stimulatory immune response.

The present disclosure also provides a compound represented by the following formula B:

Formula B

[Chemical structure of Formula B]

Wherein R is H or halogen.

In one or more embodiments, the compound of formula B is selected from the group consisting of compound a and compound b, namely:

Compound a

[Chemical structure of Compound a]

and

Compound b

[Chemical structure of Compound b]

Also provided herein are compounds of formula C below:

Lacto-XAN-PABC'     (formula C)

wherein,

X is a polar and non-polar uncharged amino acid such as alanine, proline or threonine;

A is alanine;

N is asparagine;

PABC' is —NH-phenyl-CH2-OH.

In one or more embodiments, the lactobionic acid residue linked to X via an amide bond (—C(O)—NH—).

In one or more embodiments, X and A are linked by an amide bond.

In one or more embodiments, Formula C has the structure shown by Formula C-1 below:

[Chemical structure of Formula C-1]

The present disclosure also provides the use of a compound of formula C for enhance the anticancer activity of an anticancer drug.

DETAILED DESCRIPTION OF THE PREFERRED EMBODIMENT

Figure 8:
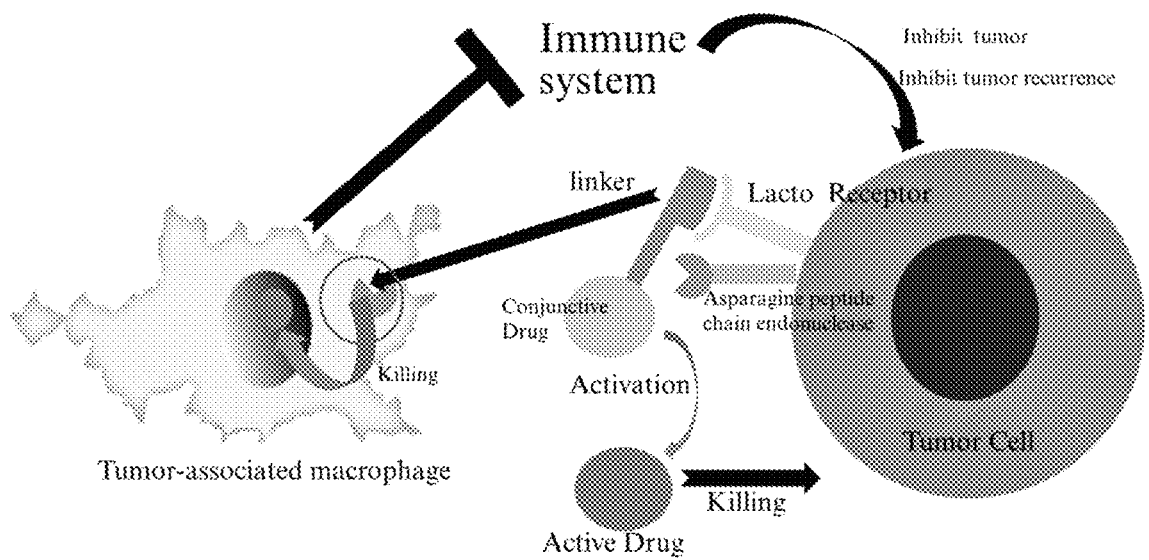
FIG. 8: A schematic diagram of the mechanism of action of the compounds of the present disclosure.

The present disclosure finds that the sialic acid glycoprotein receptor and the aspartate endopeptidase molecular receptor are co-distributed on the surface of tumor cells, and the same distribution of dual targets may be targeted for high activation of highly active compounds. The reason for this co-distribution can be used to design drugs that accumulate and remain in a co-distributed position, thereby increasing their recognition and activation efficiency for tumor cells. Based on this finding, the present inventors linked a specific asparagine endopeptidase (Legumain) substrate to a different type of saccharide, and tested the stability and enzymatic cleavage efficiency of the linker. Linkers with strong activation effects and relatively high stability were predicted. Further, the present inventors used the selected linker to link different drug molecules, thereby obtaining the compound represented by the present disclosure A. These compounds are site-directed targeting molecular to result in highly active and highly potent compounds, the mechanism of action of which is shown in FIG. 8: The site-directed targeting of the present disclosure results in high activation and high potency compounds that are efficiently activated by the same distribution of dual targets to kill The characteristics of cancer cells also have the characteristics of inhibiting M2 type tumor-associated macrophages by endocytosis and then activating anti-tumor immunity, and finally produce an activity that cures tumors, produces immunity, and causes tumors to not recur.

Accordingly, the present disclosure first provides a compound of formula C:

Lacto-XAN-PABC'          (Formula C)

Wherein X is a polar and non-polar uncharged amino acid such as alanine, valine or threonine; A is alanine; N is asparagine; PABC' is —NH-phenyl-CH2-OH.

In formula C and other compounds containing a structure of formula C herein, the lactobionic acid residues (Lacto), X and N are each linked via an amide bond, and PABC' is also linked to the asparagine residue (N) via an amide linkage.

It is to be understood that "N" in "—NH—" as a group means a nitrogen atom, and "N" as an amino acid residue means asparagine. Further, herein, the amide bond means "—C(O)—NH—".

In certain embodiments, Formula C has the structure shown by Formula C-1:

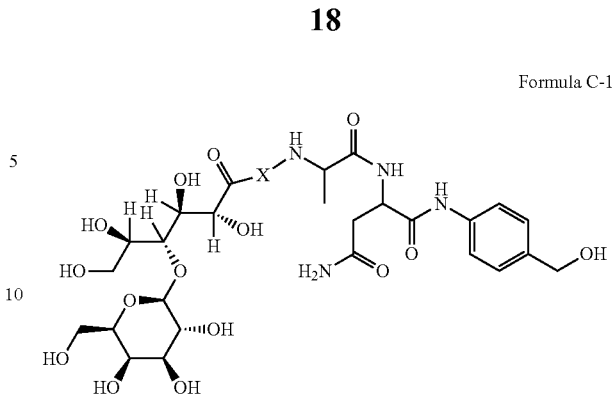

Formula C-1

The compound of formula C can be targeted as a molecule of the present disclosure to result in a linker moiety in a highly activated and highly potent compound for attachment to an active drug molecule. In particular, the targeted site targeting of the present invention results in a highly activated and highly potent compound having the structure shown in Formula A below:

Lacto-XAN-PABC-Z          (Formula A)

Wherein X is a polar and non-polar uncharged amino acid such as alanine, valine or threonine; A is alanine; N is asparagine; PABC is —NH-phenyl-CH2-O—; Z is a drug molecule of interest.

Typically, the lactobionic acid residues, XAN and PABC are each linked via an amide bond, while PABC is linked to Z by an ester bond (—O—C(O)—).

In certain embodiments, the structure of the compound of Formula A is further as shown in Formula I disclosed herein.

The drug molecule Z of interest may be selected from the sorafenib derivatives shown by the following formula B:

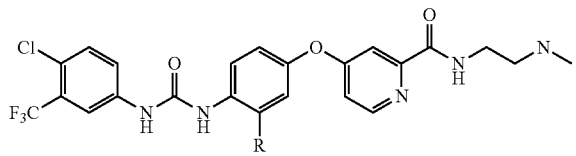

Formula B wherein R is H or halogen.

As used herein, "halogen" includes F, Cl, Br, and I.

In certain embodiments, the compound of Formula B is selected from Compound a and Compound b disclosed herein.

The drug molecule Z of interest may also be, for example, doxorubicin, darafinib, dovetinib and motesanib.

The site to which the PABC is attached can be determined based on the pharmacodynamic structure of the drug molecule of interest. It is usually connected to the PABC at a position away from its active site. The manner of connection can be in any suitable manner. Herein, the drug molecule is linked to PABC via an ester group, i.e., —O—C(O)—.

In certain embodiments of the present disclosure, X is alanine, valine or threonine, and thus Formula A may be a lactobionic acid residue—AAN-PABC-Z, a lactobionic acid residue—VAN-PABC-Z Or lactobionic acid residue—TAN-PABC-Z.

In certain embodiments of the present disclosure, X is alanine, and thus, the structure of the compound of Formula I herein can be as shown in Formula II. In other embodiments, X is a proline, and thus, the structure of the compound of Formula I herein can be as shown in Formula III. In other embodiments, X is threonine, such that the structure of the compound of Formula I herein can be as shown in Formula IV.

Exemplary compounds of Formula A or Formula I herein can be as indicated by S1-S18 as previously described.

Also included herein are pharmaceutically acceptable salts of the compounds of Formula A or Formula I herein. Examples of pharmaceutically acceptable salts include, but are not limited to, mineral acid salts and organic acid salts such as hydrochloride, hydrobromide, phosphate, sulfate, citrate, lactate, tartrate, maleate, fumarate, methane sulfonate, mandelate and oxalate; and with bases such as sodium hydroxy, tris(hydroxymethyl)aminomethane (TRIS, tromethamine) and inorganic alkali salt and organic alkali salt formed by N-methylglucamine. For example, in certain embodiments, the drug molecule Z in Formula A is a mesylate salt of darafinib, a compound of formula B, or a hydroxy propionate salt of dovetinib or the like.

The present disclosure also includes stereoisomers of the compounds of Formula A or Formula I, as well as racemates of stereoisomers. The individual enantiomers can be separated according to methods well known to those skilled in the art. It will be understood, however, that among the compounds described herein, lactobionic acid and X, A and N are preferably in their naturally occurring isomeric form.

The preparation scheme for some of the compounds herein can be as shown in Examples 1-3 herein. For example, the XAN-PABC-Z moiety of the compound of formula A can be synthesized first, followed by the lactobionic acid; alternatively, the lactobionic acid residue -XAN-PABC moiety of the compound of formula A can be synthesized first, followed by the drug molecule of interest Z is connected.

Accordingly, the present disclosure provides a pharmaceutical composition comprising a compound of formula A or a pharmaceutically acceptable salt thereof and a pharmaceutically acceptable carrier.

Pharmaceutically acceptable carriers are generally safe, non-toxic, and broadly include any known materials in the pharmaceutical industry for the preparation of pharmaceutical compositions, such as fillers, diluents, coagulants, binders, lubricants, Glidants, stabilizers, colorants, wetting agents, disintegrating agents, and the like. Suitable pharmaceutically acceptable carriers include sugars such as lactose or sucrose, mannitol or sorbitol; cellulose preparations and/or calcium phosphates such as tricalcium phosphate or dibasic calcium phosphate; starch pastes including corn starch, wheat Starch, rice starch, potato starch, gelatin, gum tragacanth, methylcellulose, hydroxypropyl methylcellulose, sodium carboxymethylcellulose and/or polyvinylpyrrolidone; silica, talc, stearic acid or a salt thereof, Such as magnesium stearate or calcium stearate and/or polyethylene glycol; and so on. In selecting a pharmaceutically acceptable carrier, it is primarily necessary to consider the mode of administration of the pharmaceutical composition, as is well known to those skilled in the art.

The pharmaceutical composition may contain a therapeutically effective amount of a compound of formula A or a pharmaceutically acceptable salt thereof. By "effective amount" is meant an amount of a component sufficient to produce the desired reaction. The specific effective amount depends on a number of factors, such as the particular condition being treated, the patient's physical condition (e.g., patient weight, age, or sex), duration of treatment, co-administered therapy (if any), and specific formula. "Effective amount" also means that the toxic or negative effect of the polypeptide of the present application is less than the positive effect brought about by this amount. In the present disclosure, a therapeutically effective amount of a compound of formula A, or a pharmaceutically acceptable salt thereof, can be comparable to a therapeutically effective amount of a conventional pharmaceutical molecule Z. In certain instances, the treatment of a compound of the present disclosure, or a pharmaceutically acceptable salt thereof, is therapeutic due to the coupling of a linker of the present disclosure (ie, a compound of formula C) with higher activation efficiency and anti-tumor effects. The effective amount is lower than the therapeutically effective amount of the conventional drug molecule Z.

The above pharmaceutical compositions can be prepared according to known pharmaceutical procedures, such as Remington's Pharmaceutical Sciences (17th edition, edited by Alfonoso R. Gennaro, Mack Publishing Company, Easton, Pa. (1985)) has a detailed record in the book.

The pharmaceutical compositions of the present disclosure may be in a variety of suitable dosage forms including, but not limited to, tablets, capsules, injections, and the like, and may be administered by any suitable route to achieve their intended purpose. For example, it can be administered by parenteral, subcutaneous, intravenous, intramuscular, intraperitoneal, transdermal, buccal, intrathecal, intracranial, nasal or topical routes. The dosage of the drug can be determined according to the age, health and weight of the patient, the type of concurrent treatment, and the frequency of treatment.

The pharmaceutical compositions of the present disclosure can be administered to any mammal, especially a human.

The compounds of formula A herein, or pharmaceutically acceptable salts or pharmaceutical compositions thereof, are especially useful for treating cancer or cancer cell metastasis. A cancer that can be treated with a compound of formula A herein, or a pharmaceutically acceptable salt or pharmaceutical composition thereof, can depend on the therapeutic activity of the drug molecule Z of interest itself. For example, it is known in the art that sorafenib is a multi-targeted tumor treatment drug, and its indications include, but are not limited to, liver tumor cells that cannot be operated or distantly metastasized, inoperable kidney tumor cells, and no treatment for radioactive iodine. Re-effective local recurrence or metastatic, progressive differentiation of thyroid patients. Adriamycin has a broad spectrum of anti-tumor, suitable for acute leukemia (lymphocytic and granulocyte), malignant lymphoma, breast cancer, bronchial lung cancer (undifferentiated small cell and non-small cell), ovarian cancer, soft tissue sarcoma Osteogenic sarcoma, rhabdomyosarcoma, Ewing sarcoma, nephroblastoma, neuroblastoma, bladder cancer, thyroid cancer, prostate cancer, head and neck squamous cell carcinoma, testicular cancer, stomach cancer and liver cancer.

Thus, a cancer of the formula A or a pharmaceutically acceptable salt or pharmaceutical composition thereof for use in therapy includes, but is not limited to, liver cancer, kidney cancer, thyroid cancer, colorectal cancer, bladder cancer, brain cancer, breast cancer, cervical cancer, rectal cancer, esophageal cancer, lung cancer (such as bronchial lung cancer, including undifferentiated small cell and non-small cell), nasopharyngeal cancer, pancreatic cancer, prostate cancer, skin cancer, stomach cancer, uterine cancer, ovarian cancer, testicular cancer, Blood cancer (eg chronic or acute leukemia, including lymphocytic and granulocyte leukemia), malignant lymphoma, fibrosarcoma, soft tissue sarcoma, osteosarcoma, rhabdomyosarcoma, Ewing's sarcoma, nephroblastoma, neuroblastoma, Thyroid cancer and squamous cell carcinoma of the head and neck. The compounds of formula A herein, or pharmaceutically acceptable salts or pharmaceutical compositions thereof, are also useful in the treatment of these cancer cell metastases that accompany these cancers.

In certain aspects, the compounds of Formula A, or a pharmaceutically acceptable salt or pharmaceutical composition thereof, can also stimulate T cell proliferation and invasion of the foci, inhibit tumor-associated macrophages, and/or promote a stimulatory immune response.

Accordingly, the present disclosure provides a method of treating cancer or cancer cell metastasis comprising administering to a subject in need thereof a therapeutically effective amount of a compound of formula A, or a pharmaceutically acceptable salt or pharmaceutical composition thereof, disclosed herein. The cancer or cancer cell metastasis is as described above.

In certain aspects, the present disclosure also provides a method of stimulating T cell proliferation and invasion of a lesion, inhibiting tumor-associated macrophages, and/or promoting a stimulatory immune response, the method comprising administering to a subject in need thereof therapeutically effective An amount of a compound of formula A as disclosed herein, or a pharmaceutically acceptable salt or pharmaceutical composition thereof.

The "object" of interest can be any mammal, especially a human.

Also provided is the use of a compound of the formula A or a pharmaceutically acceptable salt thereof for the manufacture of a medicament for the treatment of cancer or cancer cell metastasis, or for the preparation of an immunotherapeutic medicament. The cancer or cancer cell metastasis is as described above; the immunotherapeutic agent can be used to stimulate T cell proliferation and invasion of the lesion, inhibit tumor-associated macrophages, and/or promote a stimulatory immune response.

Also provided is a compound of formula A, or a pharmaceutically acceptable salt thereof, of the present disclosure for use in treating cancer or cancer cell metastasis, or for stimulating T cell proliferation and invasion of a tumor, inhibiting tumor-associated macrophages and/or promote stimulation of the immune response.

It is to be understood that the various aspects, embodiments, and features of the specific embodiments described herein can be arbitrarily combined to form a preferred embodiment. Thus, for example, although the above disclosure discloses only a compound of formula A or a pharmaceutically acceptable salt thereof, any of the compounds disclosed herein falling within the scope of formula A, such as compounds of formulas I, II, III and IV, or Compounds S1-S18 can be used in the treatment of any of the cancer or cancer cell metastasis specifically disclosed above.

The present application is further described below in conjunction with specific embodiments. Unless otherwise stated, the following examples will employ conventional methods of chemistry, biochemistry, and immunology known to those skilled in the art.

These techniques are fully explained in the literature. In addition, the various materials and reagents used in the examples are known and/or conventional materials and reagents unless otherwise stated.

Example 1: Synthesis of Compounds S1, S7 and S13

Compounds S1, S7 and S13 were synthesized by the following procedure, wherein X is alanine:

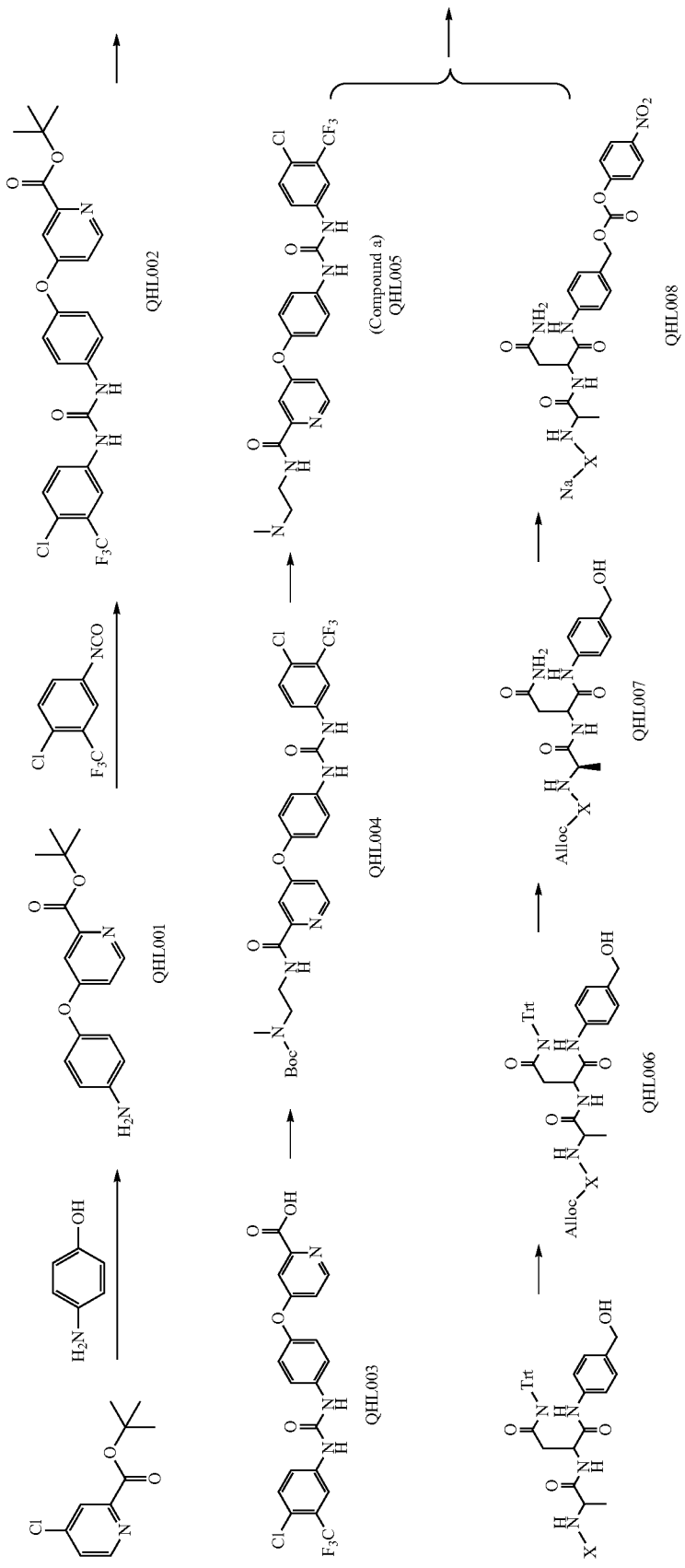

-continued
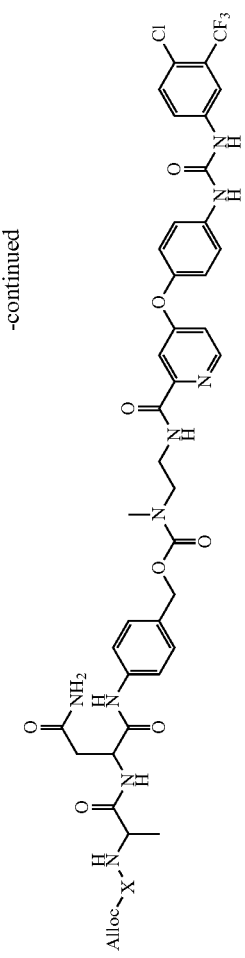
QHL009
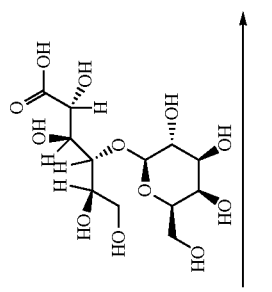
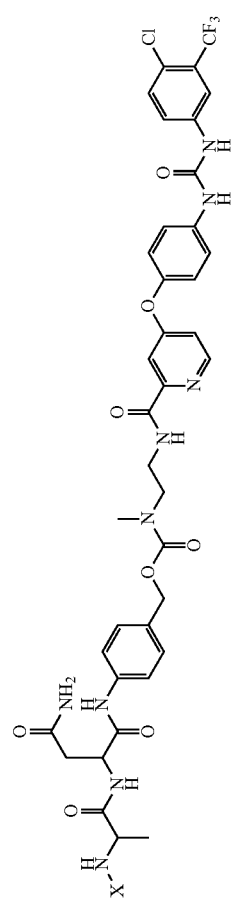
QHL010
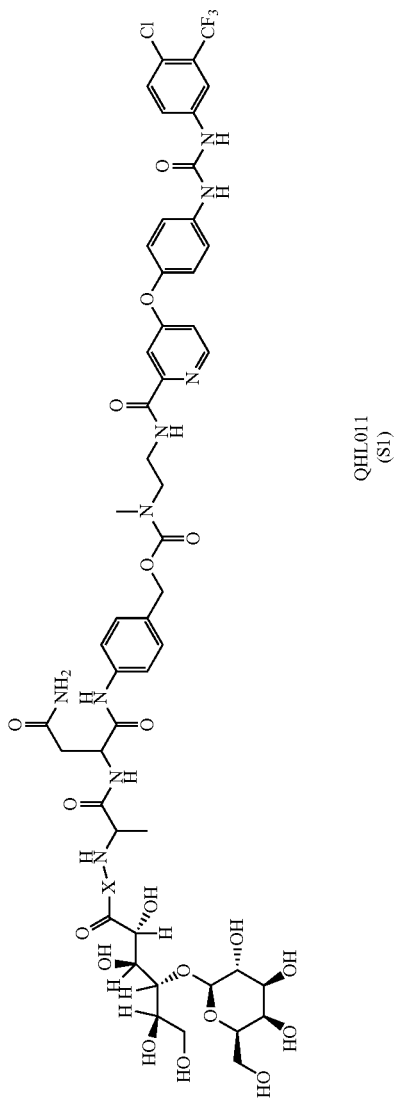
QHL011
(S1)

Synthesis of QHL001

DMF (40 ml), p-aminophenol (5 g, 45.8 mmol), potassium tert-butoxide (5.35 g, 47.7 mmol) were added in a 100 ml single-neck flask. After stirring for 30 minutes, tert-butyl 4-chloropyridine-2-carboxylate (11.75 g, 55 mmol) was added. After stirring at room temperature for 5 minutes, the temperature was raised to 80° C. and allowed to react overnight. DMF was evaporated under reduced pressure, and the residue was dissolved in dichloromethane, washed with water, and evaporated. The organic phase was dried, dried and purified by silica gel column chromatography (dichloromethane:methanol=80:1 to 10:1) to afford white solid QHL001 (7.86 g, yield: 60%).

Synthesis of QHL002

In a 100 ml single-necked flask, DCM (30 ml), QHL001 (7.80 g, 27.3 mmol) was added in sequence, and after stirring for 5 minutes, the system was cooled to 0° C. with an ice salt bath, and 4-chloro-3-trifluorobenzene was added dropwise. Phenyl isocyanate (7.0 g, 32.8 mmol). After the addition was completed, the ice salt bath was removed, allowed to warm to room temperature, and allowed to react overnight. Add 50 ml of water, extract and separate. The organic phase was dried, and purified by silica gel column chromatography (dichloromethane:methanol=50:1 to 10:1) to afford brown solid QHL 002 (10.54 g, yield 76%).

Synthesis of QHL003

In a 100 ml single-necked flask, DCM (15 ml), trifluoroacetic acid (15 ml), QHL002 (10.5 g, 20.7 mmol), triethyl silane (2.5 ml) were sequentially added and stirred at room temperature until QHL002 was completely reacted. The solvents were removed by evaporation under reduced pressure. The residue was purified by silica gel column chromatography by volume ratio, dichloromethane:methanol=50:1 to 5:1), a white solid QHL003 (7.47 g, yield 80%) was obtained.

Synthesis of QHL004

DMF (10 ml), QHL003 (417 mg, 0.92 mol), N—BOC—N-methyl ethylenediamine (200 mg, 1.25 mmol), HATU (420 mg, 1.10 mmol) were added in a 50 ml single-necked bottle. After stirring for 5 minutes, DIPEA (0.5 ml, 2.76 mmol) was added dropwise. Stir at room temperature until QHL003 was completely reacted. DMF was evaporated under reduced pressure, and the crude product was dissolved in ethyl acetate and washed with water. The organic phase was dried, and purified by silica gel column chromatography (dichloromethane:methanol=50:1 to 20:1) to obtain light yellow solid QHL004 (454 mg, yield 83%).

Synthesis of QHL005

Compound QHL004 (450 mg, 0.764 mmol) was dissolved in DCM (10 mL). Stir at room temperature until QHL004 was completely reacted. The solvent was evaporated, and the residue was purified by silica gel column chromatography (dichloromethane:methanol=30:1 to 10:1) to obtain light yellow solid QHL005 (340 mg, yield 90%).

Synthesis of QHL006

In a 100 ml single-necked flask, L-Ala-L-Ala-L-Asn(Trt)-PABC (6.21 g, 10 mmol), DMF (20 ml), DIPEA (1.29 g, 10 mmol) was sequentially added. After stirring at room temperature for 5 minutes, the system was cooled to 0° C. by ice salt bath. Allyl chloroformate (1.21 g, 10 mmol) was added slowly and stirred at room temperature overnight. After the completion of the reaction, DMF was evaporated under reduced pressure, and the residue was purified by silica gel column chromatography (dichloromethane:methanol=50:1 to 10:1) to afford white solid QHL006 (5.0 g, yield 71%).

Synthesis of QHL007

In a 100 ml single-necked flask, DCM (15 ml), trifluoroacetic acid (15 ml), QHL 006 (5.0 g) were sequentially added, and the mixture was stirred at room temperature until QHL012 was completely reacted. Then DCM and trifluoroacetic acid were removed by rotary evaporation, and the residue was slurried with methyl tert-butyl ether for 1 h. Filter and collect solids. The solid was dissolved in Methanol (30 mL), DIPEA (15 ml) was added, and the mixture was stirred at room temperature for 2 h, the solvent was dried to obtain a crude product. The crude product was again slurried with methyl tert-butyl ether for 1 h, filtered and dried to obtain QHL007 (2.75 g, yield 92%).

Synthesis of QHL008

In a 100 ml single-necked flask, DMF (15 ml), QHL007 (2.75 g, 5.94 mmol), 4,4-dinitrodiphenyl carbonate (3.54 g, 11.6 mmol), DIPEA (1.13 g, 8.76 mmol) were sequentially added, stir at room temperature until QHL007 was completely reacted. After the completion of the reaction, DMF was evaporated under reduced pressure, and the residue was purified by silica gel column chromatography (dichloromethane:methanol=50:1 to 10:1) to obtain white solid QHL 008 (2.43 g, yield 65%).

Synthesis of QHL009

In a 50 ml single-mouth bottle, DMF (10 ml), QHL005 (508 mg, 1 mmol), QHL008 (629 mg, 1 mmol) were sequentially added. After stirring for 5 minutes, DIPEA (387 mg, 3 mmol) was added dropwise and the mixture was stirred at room temperature for 2 h. The DMF was evaporated under reduced pressure, and the crude product was purified and purified by silica gel column chromatography (dichloromethane:methanol=50:1 to 10:1) to afford white solid QHL 009 (698 mg, yield: 70%).

Synthesis of QHL010

In a 50 ml single-mouth bottle, DMF (10 ml), QHL009 (310 mg, 0.31 mmol), acetic acid (274 mg, 4.65 mmol), triphenylphosphine palladium (72 mg, 0.062 mmol), tri-n-butyltin hydride (1.17) were sequentially added. g, 4.03 mmol), after replacing the nitrogen, stirring at room temperature until the reaction of QHL009 was complete. After completion of the reaction, DMF was evaporated under reduced pressure, and the crude product was purified by silica gel column chromatography (dichloromethane:methanol=50:1 to 10:1) to afford white solid QHL 010 (175 mg, yield: 62%).

Synthesis of S1 (Lacto-AAN-PABC-compound a)

The lactobionic acid (3.8 g, 10 mmol) was dissolved in anhydrous methanol (100 ml), and the mixture was heated up to reflux. After 24 hours of reaction, cooled to room temperature, QHL010 (175 mg, 0.192 mmol) was dissolved in anhydrous methanol (10 ml), and added dropwise to the above-mentioned lactic acid in methanol. After the dropwise addition was completed, the system was heated up to 60° C. and allowed to react overnight. The reaction solution was dried by rotary evaporation. The resultant crude product was purified by reversed phase preparative column chromatography to afford white solid S1 (91 mg, yield: 36%).

Compounds S7 (Lacto-VAN-PABC-compound a) and S13 (Lacto-TAN-PABC-compound a) were prepared by a method similar to that of S1 synthesis, using different amino acid residues.

Example 2: Synthesis of Compounds S2, S8 and S14

Compounds S2, S8 and S14 were synthesized using the following procedure, wherein X is alanine:

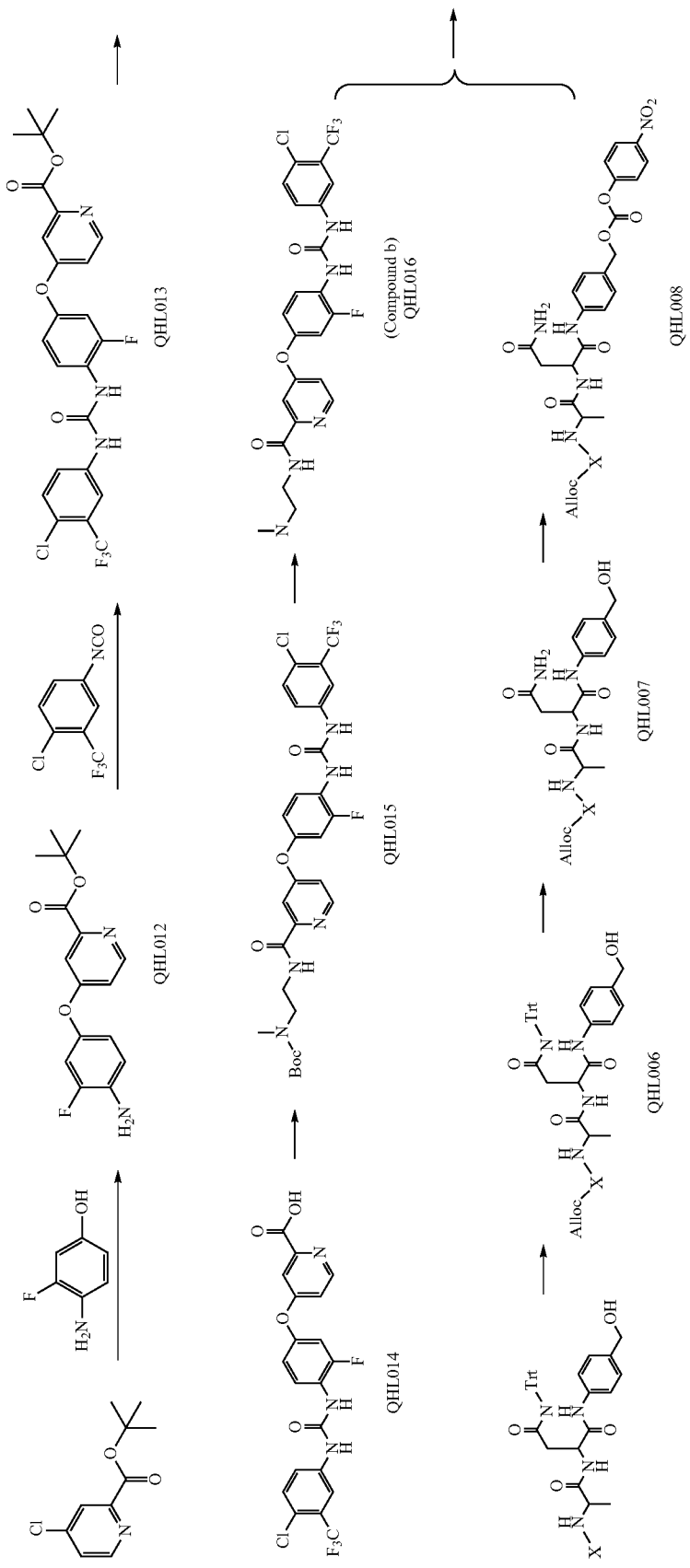

-continued
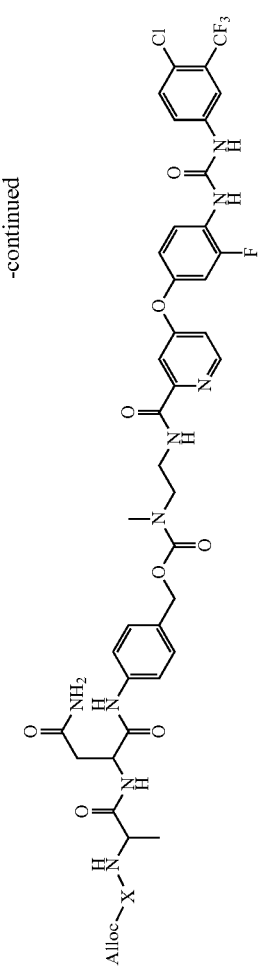
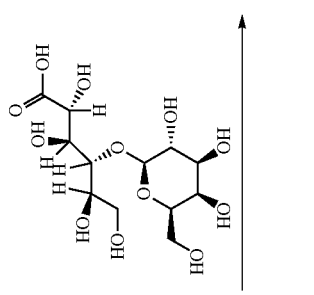
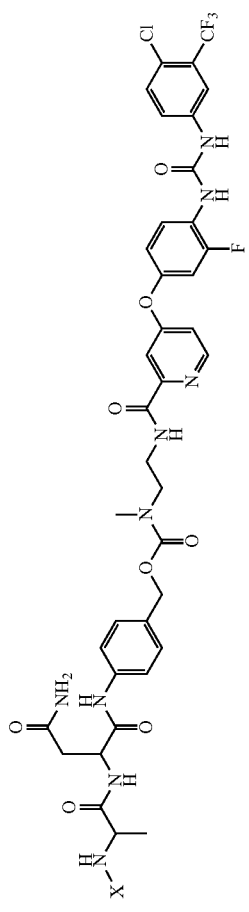
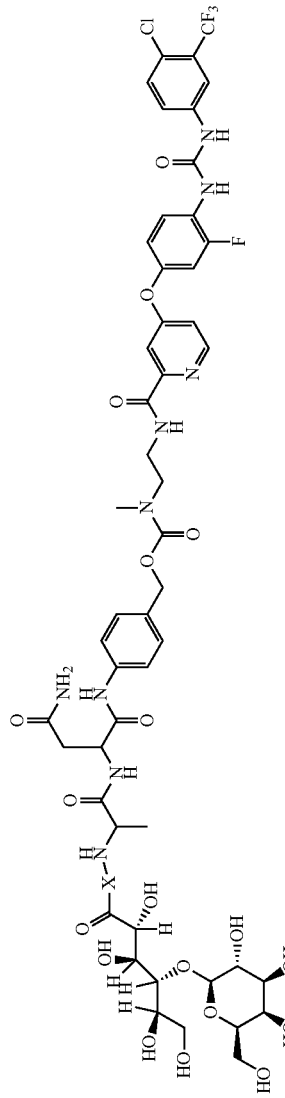

Synthesis of QHL012

DMF (40 ml), 4-amino-3-fluoro-phenol (5.8 g, 45.8 mmol), potassium t-butoxide (5.35 g, 47.7 mmol) were sequentially added to a 100 ml single-necked flask. After stirring for 30 minutes, tert-butyl 4-chloropyridine-2-carboxylate (11.75 g, 55 mmol) was added. After stirring at room temperature for 5 minutes, the temperature was raised to 80° C. and allowed to react overnight. DMF was evaporated under reduced pressure, and the residue was dissolved in dichloromethane, washed with water, and evaporated. The organic phase was dried, and purified by silica gel column chromatography (dichloromethane:methanol=80:1 to 10:1) to afford white solid QHL 012 (9.7 g, yield: 70%).

Synthesis of QHL013

In a 100 ml single-necked flask, DCM (30 ml), QHL012 (8.30 g, 27.3 mmol) were added in sequence, and after stirring for 5 minutes, the system was cooled to 0° C. with an ice salt bath, and 4-chloro-3-trifluorobenzene phenyl isocyanate (7.0 g, 32.8 mmol) was added dropwise. After the addition was completed, the ice salt bath was removed, allowed to warm to room temperature, and react overnight. Add 50 ml of water, extract and separate. The organic phase was dried, and purified by silica gel column chromatography (dichloromethane:methanol=50:1 to 10:1) to give a brown solid QHL 013 (11.2 g, yield 75%).

Synthesis of QHL014

In a 100 ml single-necked flask, DCM (15 ml), trifluoroacetic acid (15 ml), QHL013 (11.2 g, 20.7 mmol), triethyl silane (2.5 ml) were added sequentially, and the mixture was stirred at room temperature until QHL013 was completely reacted. After the completion of the reaction, the reaction mixture was evaporated under reduced pressure, The crude product was separated and purified using silica gel column chromatography (dichloromethane:methanol=50:1 to 5:1) to afford white solid QHL 014 (7.92 g, yield 80%).

Synthesis of QHL015

DMF (20 ml), QHL 014 (4.42 g, 9.2 mmol), N—BOC—N-methyl ethylenediamine (2.00 g, 12.5 mmol), HATU (4.20 g, 11 mmol) was added in a 50 ml single-necked flask. After stirring for 5 minutes, DIPEA (5 ml, 27.6 mmol) was added dropwise. Stir at room temperature until QHL014 is completely reacted. DMF was evaporated under reduced pressure, and the crude product was dissolved in ethyl acetate and washed with water. The organic phase was dried and purified by silica gel column chromatography (dichloromethane:methanol=50:1 to 20:1) to obtain light yellow solid QHL 015 (4.81 g, yield 80%).

Synthesis of QHL016

Compound QHL015 (4.80 g, 7.64 mmol) was dissolved in DCM (10 mL), trifluoroacetic acid (10 ml) was added. Stir at room temperature until QHL015 was completely reacted. The solvent was evaporated, and the residual solid was purified by silica gel column chromatography (dichloromethane:methanol=30:1 to 10:1) to give pale yellow solid QHL016 (3.60 g, yield: 90%).

Synthesis of QHL017

In a 50 ml single-necked flask, DMF (10 ml), QHL016 (670 mg, 1.28 mmol), QHL008 (965 mg, 1.54 mmol) were sequentially added. After stirring for 5 minutes, DIPEA (1.4 ml, 7.68 mmol) was added dropwise, and the mixture was stirred at room temperature for 3 h. The DMF was evaporated under reduced pressure, and the crude product was purified by silica gel column chromatography (dichloromethane:methanol=50:1 to 15:1) to obtain white solid QHL 017 (1.0 g, yield: 77%).

Synthesis of QHL018

In a 50 ml single-necked flask, DMF (10 ml), QHL017 (500 mg, 0.49 mmol), acetic acid (0.42 ml, 7.39 mmol), triphenylphosphine palladium (116 mg, 0.10 mmol), tri-n-butyltin hydride (1.75 ml, 6.37 mmol) were added sequentially, after replacing nitrogen, stir at room temperature until QHL017 was completely reacted. After the completion of the reaction, DMF was evaporated under reduced pressure, and the crude product was purified by silica gel column chromatography (dichloromethane:methanol=50:1 to 10:1) to give white solid QHL 018 (300 mg, yield: 65%).

Synthesis of S2

The lactobionic acid (3.8 g, 10 mmol) was dissolved in anhydrous methanol (100 ml), and the mixture was heated up to reflux. After 24 hours of reaction, cooled to room temperature, QHL010 (175 mg, 0.188 mmol) was dissolved in anhydrous methanol (10 ml), and added dropwise to the above-mentioned lactic acid in methanol. After the dropwise addition was completed, the system was heated up to 60° C. and allowed to react overnight. The reaction solution was dried by rotary evaporation. The resultant crude product was purified by reversed phase preparative column chromatography to afford white solid S2 (102 mg, yield: 42%).

Compounds S8 (Lacto-VAN-PABC-compound b) and S14 (Lacto-TAN-PABC-compound b) were prepared by a method similar to the S2 synthesis by ligation with different amino acid residues.

Example 3: Synthesis of Compounds S3-S6, S9-S11 and S15-S18

The compounds S3-S6, S9-S11 and S15-S18 were synthesized by the following scheme, wherein X is alanine, threonine or valine.

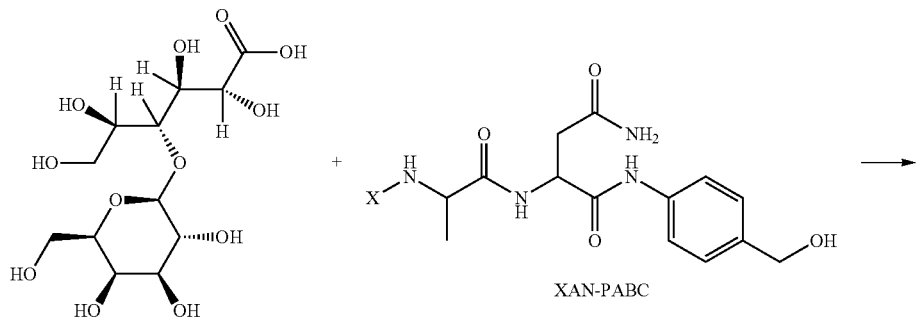

XAN-PABC

-continued

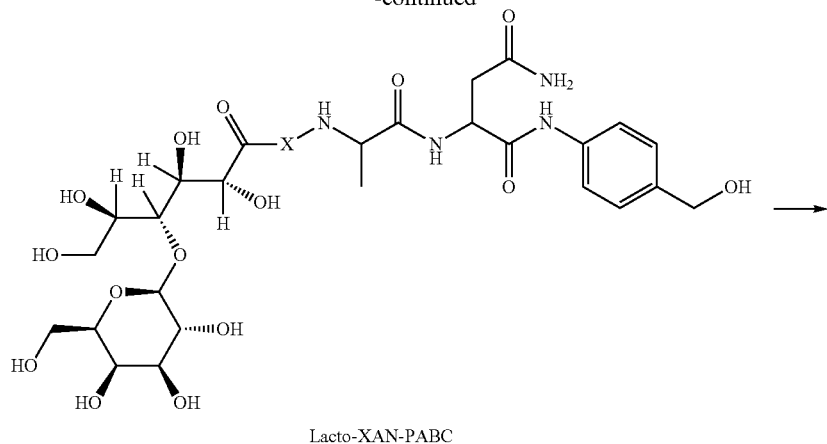

Lacto-XAN-PABC

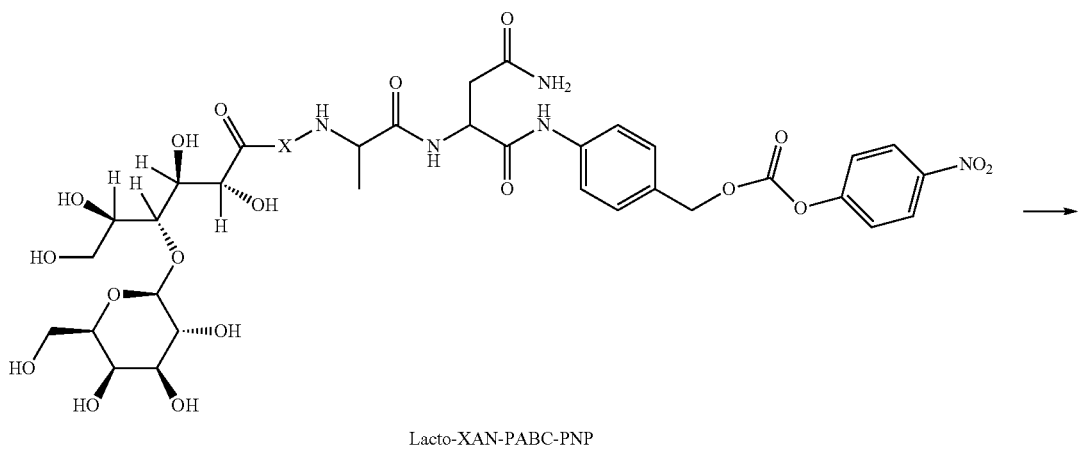

Lacto-XAN-PABC-PNP

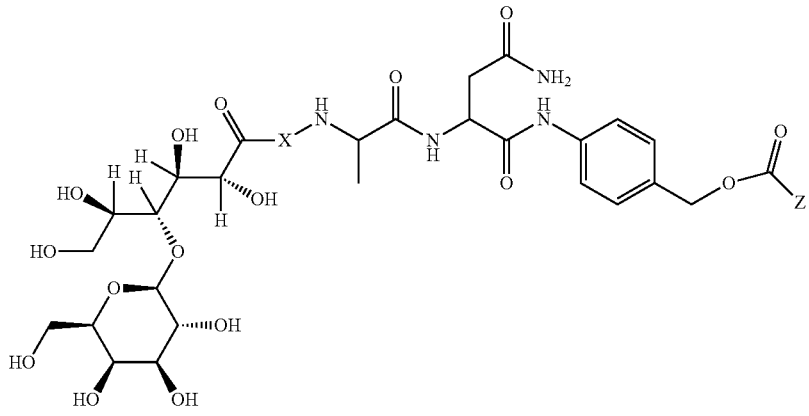

Lacto-XAN-PABC-Z

Specifically, the amino terminus of X in XAN-PABC is first reacted with the carboxyl group of lactobionic acid to form a site-directed targeting linker (Lacto-XAN-PABC). The Lacto-XAN-PABC is then activated to generate Lacto-XAN-PABC-PNP. Compound Z is subjected to a nucleophilic reaction with Lacto-XAN-PABC-PNP with an amino group contained in its structure to obtain a compound Lacto-XAN-PABC-Z.

The synthesis of these compounds is illustrated below by taking compound S3 as an example:

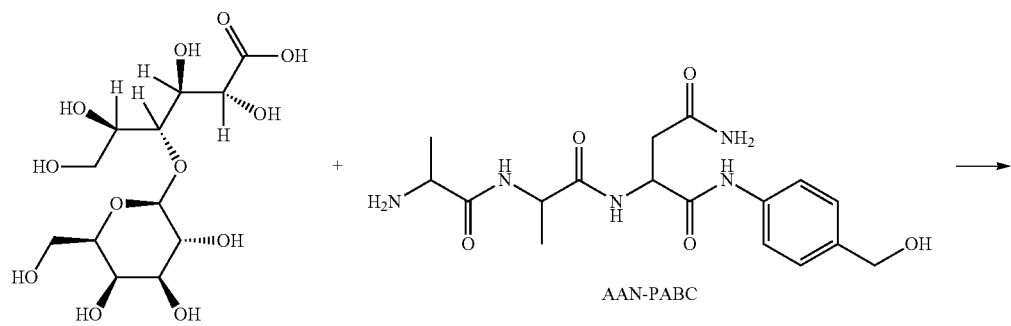
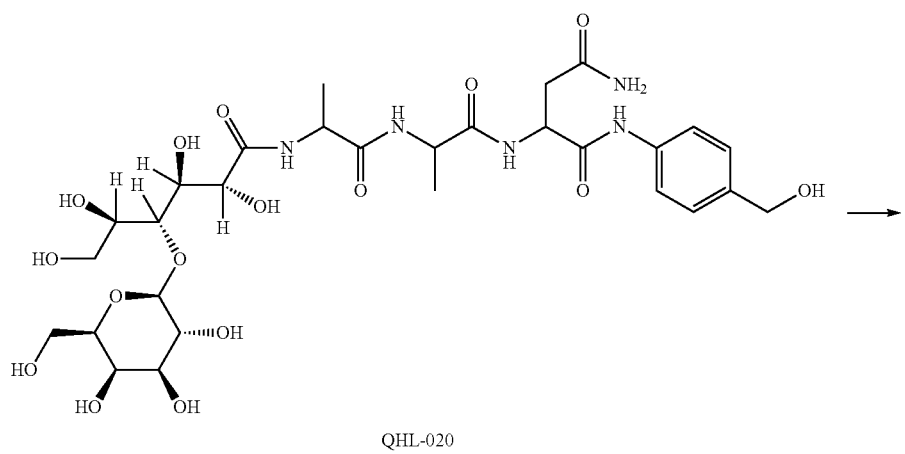
QHL-020
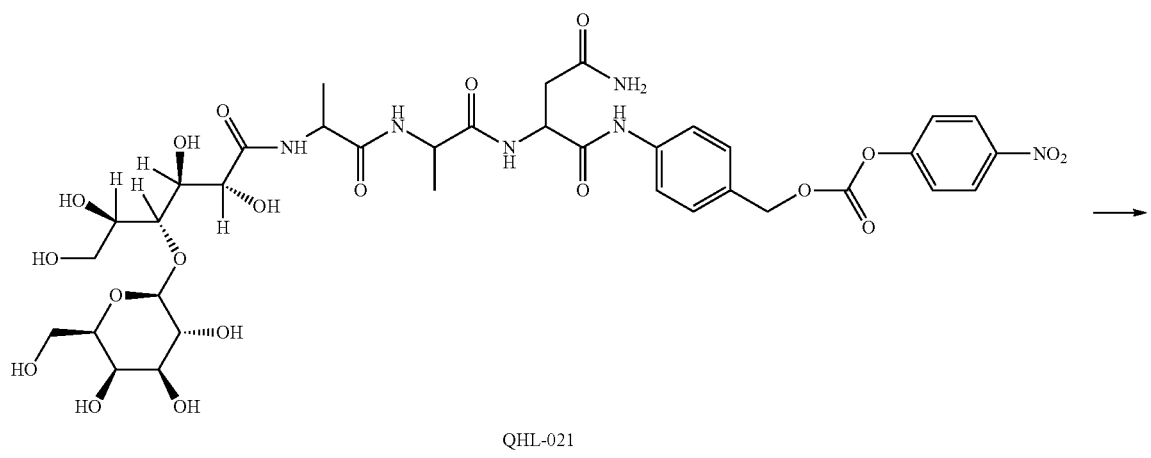
QHL-021

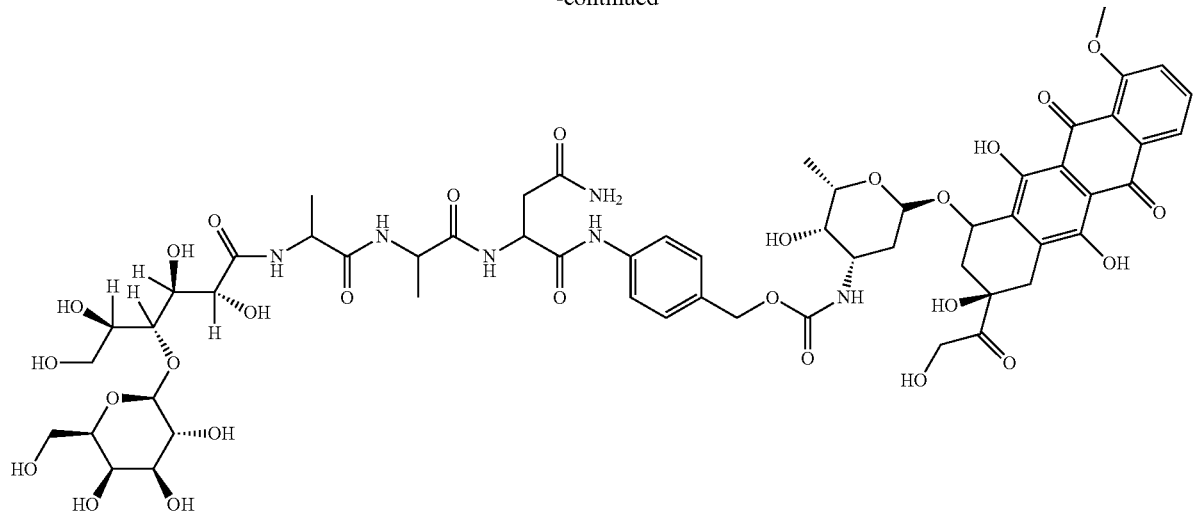

QHL-022 S3

Synthesis of QHL020

The lactobionic acid (3.8 g, 10 mmol) was dissolved in anhydrous methanol (100 ml), and the mixture was heated up to reflux. After 24 hours of reaction, cooled to room temperature, L-Ala-L-Ala-L-Asn-PABC (760 mg, 2.0 mmol) was dissolved in anhydrous methanol (10 ml), and added dropwise to the above-mentioned lactic acid in methanol. After the dropwise addition was completed, the system was heated up to 60° C. and allowed to react overnight. The reaction solution was dried by rotary evaporation. The resultant crude product was purified by reversed phase preparative column chromatography to afford white solid QHL020 (650 mg, yield: 45%).

Synthesis of QHL021

DMF (15 ml), QHL020 (650 mg, 0.90 mmol), 4,4-dinitrodiphenyl carbonate (354 mg, 1.16 mmol), DIPEA (113 mg, 0.88 mmol). After the completion of the reaction, DMF was evaporated under reduced pressure, and the residue was purified by silica gel column chromatography (dichloromethane:methanol=25:1 to 3:1) to afford white solid QHL021 (243 mg, yield 30%).

Synthesis of S3

In a 50 ml single-necked flask, DMF (10 ml), QHL021 (180 mg, 0.2 mmol), and doxorubicin hydrochloride (192 mg, 0.33 mmol) were sequentially added. After stirring for 5 minutes, DIPEA (194 mg, 1.5 mmol) was added dropwise. The DMF was evaporated under reduced pressure, and the crude product was purified by reversed phase preparative column chromatography to afford QHL 022 red solid (127 mg, yield: 49%).

When Z is doxorubicin, the linked amino acids are changed, respectively, to obtain Examples S9, S15;

When Z is darafenib, the linked amino acids are changed, respectively, to obtain examples S4, S10, S16;

When Z is dovetinib, the linked amino acids are changed to obtain Examples S5, S11, and S17, respectively;

When Z is motesanib, the linked amino acids are altered to obtain Examples S6, S12, S18, respectively.

The mass spectrometry (MS) detection results confirmed that the S1-S18 compound had a molecular weight as shown in Table 1 below, which was consistent with the molecular weight predicted by the structural calculation.

TABLE 1

| Number | Mass spectrometry | Molecular weight | appearance | Production (mg) | Yield |
|---|---|---|---|---|---|
| S1 | 1253 | 1253.18 | White solid | 91 | 36% |
| S2 | 1272 | 1271.57 | white solid | 102 | 42% |
| S3 | 1289 | 1289.20 | red solid | 127 | 49% |
| S4 | 1263 | 1263.23 | white solid | 102 | 40% |
| S5 | 1135 | 1135.09 | white solid | 114 | 49% |
| S6 | 1117 | 1117.12 | white solid | 70 | 31% |
| S7 | 1282 | 1281.63 | white solid | 103 | 40% |
| S8 | 1300 | 1299.62 | white solid | 110 | 45% |
| S9 | 1317 | 1317.26 | red solid | 114 | 43% |
| S10 | 1291 | 1291.29 | white solid | 117 | 45% |
| S11 | 1163 | 1163.14 | white solid | 96 | 41% |
| S12 | 1145 | 1145.17 | white solid | 65 | 28% |
| S13 | 1284 | 1283.60 | white solid | 85 | 30% |
| S14 | 1302 | 1301.59 | white solid | 92 | 37% |
| S15 | 1319 | 1319.23 | red solid | 108 | 41% |
| S16 | 1293 | 1293.26 | white solid | 97 | 37% |
| S17 | 1165 | 1165.12 | white solid | 101 | 43% |
| S18 | 1147 | 1147.15 | white solid | 56 | 25% |

Example 4: Synthetic Screening of Site-Directed Targeting of Molecules Leads to Highly Activated Linker Components The tumor tissue-specific activation site is a short peptide, because the enzyme activity center of the aspartic endopeptidase is located at the bottom of the balloon-like invagination, and the cleavage site needs to be close to the enzyme activity center. Whether or not the point has steric hindrance becomes very important.

The specific aspartic acid endopeptidase (Legumain) enzyme substrate peptide was ligated to different types of carbohydrates, and the stability and enzymatic cleavage efficiency of the resulting linker were tested, and a strong activation was predicted. The linker with relatively high effect and stability, the results are shown in Table 2 below.

TABLE 2

| carbohydrate | Product linked to the enzyme substrate peptide | stability | Digestion efficiency |
|---|---|---|---|
| PEG monomer | PEG-Ala-Ala-ASN-PABC | 97.6% | 68.6% |
| Glucose (structure) | Glucose-imine-Ala-Ala-Asn-PABC (structure) | 89.6% | 25.5% |
| Xylan (structure) | Xylan-imine-Ala-Ala-Asn-PABC (structure) | 78.9% | 60.4% |
| Sorbose (structure) | Sorbose-imine-Ala-Ala-Asn-PABC (structure) | 85.5% | 35.8% |
| Lactobionic acid (structure) | Lactobionic acid-Ala-Ala-Asn-PABC (structure) | 98.4% | 95.7% |

The above results indicate that the lactobionic acid-AAN-PABC of the present invention not only does not affect the activation efficiency, but also promotes the activation efficiency and stability as compared with PEG-Ala-Ala-ASN-PABC.

Figure 1:
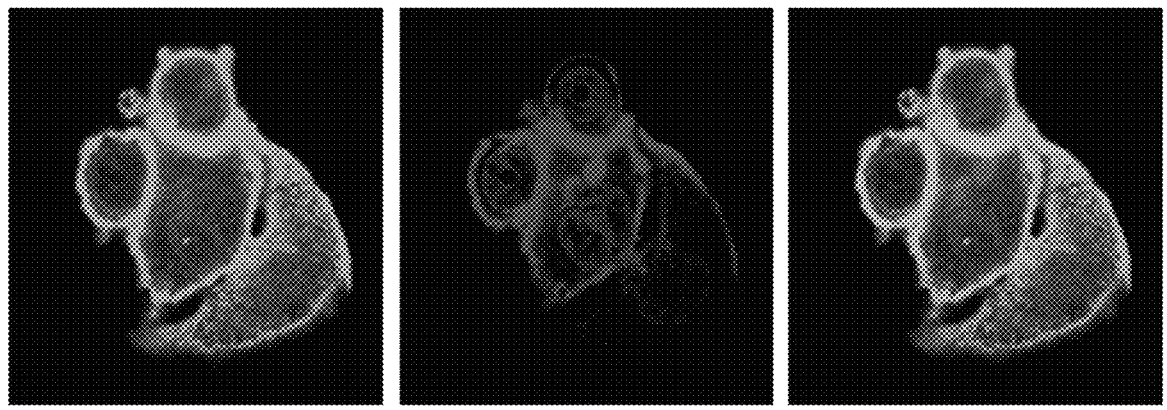
FIG. 1: Site-directed targeting of molecules leads to the same distribution of highly active and highly efficient molecular receptors on the surface of tumor cells. Fluorescence confocal microscopy for detection of antibody-tagged MDA-MB435 tumor cells, aspartate endopeptidase (left 1, green), sialoglycoprotein receptor (left 2, red), DAPI (blue), the two figures merge and are yellow (left 3).

Example 5: Cellular Distribution Characteristics of Sialic Acid Glycoprotein Receptor and Aspartate Endopeptidase The inventors have intensively studied that the sialic acid glycoprotein receptor and the aspartic endopeptidase molecular receptor are co-distributed on the surface of tumor cells. Specifically, in the immunofluorescence staining of MDA-MB435 breast cancer tumor cells, the corresponding antibody-labeled sialoglycoprotein receptor and aspartic endopeptidase were detected by fluorescence confocal microscopy, and DAPI was used for nuclear staining. As a result, as shown in FIG. 1, the distribution of the sites of the sialic acid glycoprotein receptor and the aspartic endopeptidase was the same. This co-distribution feature allows the compounds of the invention to accumulate and remain in a co-distributed position, thereby increasing their efficiency in recognition and activation of tumor cells.

Figure 2:
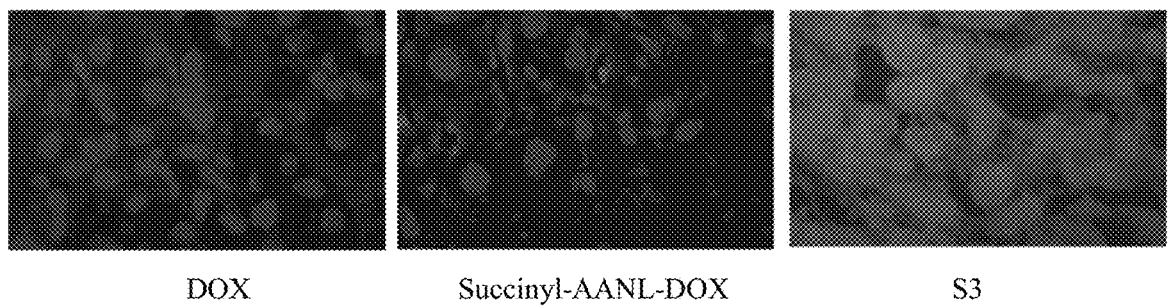
FIG. 2: Compared with Succinyl-AANL-DOX, S3 has more tumor tissue distribution and penetration after intravenous injection.

Example 6: Tissue Distribution Characteristics of the Compounds of the Invention Since DOX, Succinyl-AANL-DOX and S3 have autofluorescence, they can be detected by fluorescence microscopy in tumor tissues. 10 μmol/kg of DOX, Succinyl-AANL-DOX and S3 were injected intravenously. After 12 hours, the drug distribution image of the tumor tissue sections and the fluorescence intensity of the tumor tissue homogenate were measured. Nuclear staining was performed using DAPI. The result is shown in FIG. 2. The results showed that S3 had more tumor tissue distribution and penetration after intravenous injection than Succinyl-AANL-DOX, indicates that the molecular site-targeting function of S3 enables it to simultaneously target both sialic acid glycoprotein receptor and aspartate endopeptidase, thus, it has a strong retention effect on the tumor site than Succinyl-AANL-DOX.

Example 7: Synthesis of Sorafenib Derivatives

Figure 3:
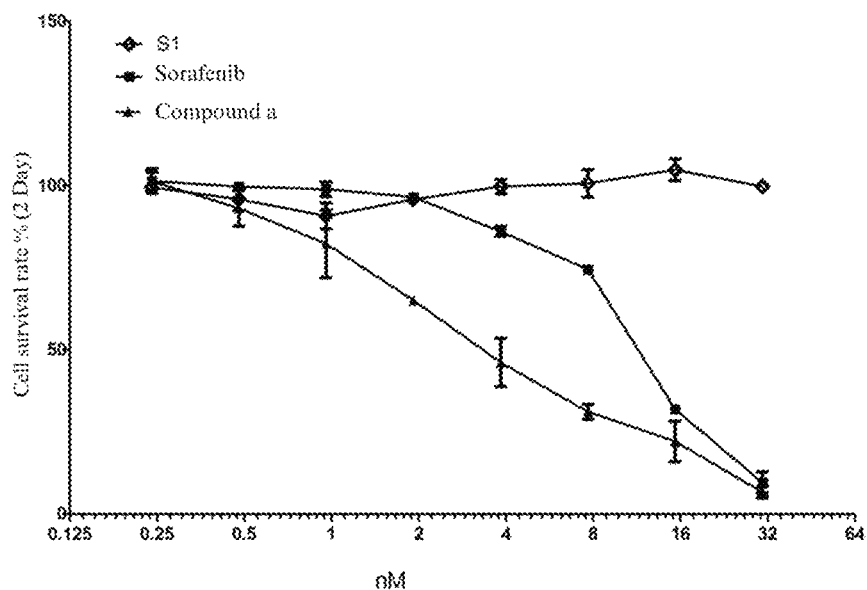
FIG. 3: Toxic effects of S1, sorafenib and compound a on Heg2 tumor cells.

Sorafenib does not have the potential to be coupled to a compound of formula II of the invention. In order to solve this dilemma, the present invention performs allosteric synthesis and screening of the ortho-carboxamide group of the pyridine ring in the sorafenib molecule, and obtains a special compound which satisfies both the structure-activity relationship and the release effect. That is, compound a and compound b). The stability and cell viability experiments of compound a and compound b showed that compound a and compound b were stable in weak acid, weak base and neutral buffer system, did not degrade, and inhibited cancer cells better than the positive control drugs sorafenib and regorafenib (FIG. 3).

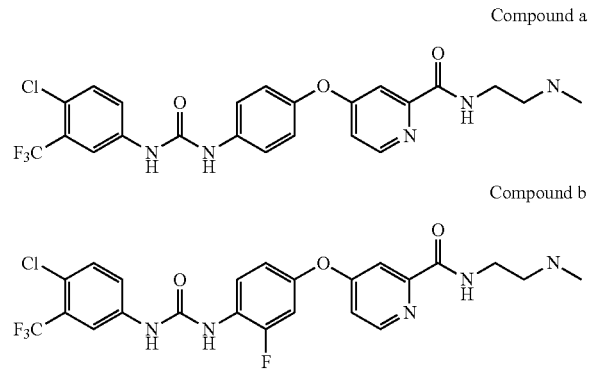

Compound a

Compound b

Example 8: Antitumor Cytotoxicity of S1 and Compound a

Collect logarithmic Heg2 cells, adjust the cell suspension concentration, add 140 ul per well, and plate to adjust the density of the cells to be tested ~5000/well; 5% $CO_2$, incubate at 37° C. overnight, until the cell monolayer is covered with the bottom of the well (96) Condensate bottom plate), adding continuous concentration gradient to give different concentrations of compound S1, compound a and sorafenib, the drug set 9 concentration gradients, 10 ul per well, set 3 duplicate wells; 5% $CO_2$, 37° C. PH6 0.5 incubation for 48 hours, observed under an inverted microscope; 20 μl of MTT solution (5 mg/ml, i.e. 0.5% MTT) was added to each well and incubation was continued for 4 h. The culture was terminated, and the culture solution in the well was carefully aspirated; 100 ul of dimethyl sulfoxide was added to each well, and shaken on a shaker at a low speed for 10 min to dissolve the crystals sufficiently. The absorbance of each well was measured at an enzyme-linked immunosorbent detector at OD490 nm. At the same time, zero adjustment holes (medium, MTT, dimethyl sulfoxide), control group (cell, same concentration of drug dissolution medium, medium, MTT, dimethyl sulfoxide) were set. The toxicity of the compound to normal hepatocytes was analyzed after the test, and the results are shown in FIG. 3. FIG. 3 shows that compound a is more toxic than sorafenib after 2 days of administration of different concentrations of compound. S1, by coupling the linker, becomes a drug that is non-toxic to normal cells.

Example 9: Relative Activation Characteristics of Compounds

The sample compound and a portion of the control compound (herein, all of the control compounds can be synthesized by a method similar to that described in Examples 1-3) were uniformly diluted 10-fold to 1 mg/ml with the enzyme-digesting solution. In this experiment, 1 mg/ml of the sample compound was added to the aspartic endopeptidase (1 μmol/L, pH 6.0) at 37° C. for 2 hours. After the reaction, the enzyme digest was able to release the enzyme-digested product. The decrease in the compound and the increase in the product were examined by HPLC to compare the enzyme activation efficiency (the ratio of the product released by the enzyme cleavage to the original compound). The results are shown in Table 3 below.

TABLE 3

| Activation efficiencies of the compounds of the invention and a portion of the control compounds | |
|---|---|
| Compound | Activation efficiencies (%) |
| C1: AANL-Compound a | 1.8 (Not activated) |
| C2: AAN-PABC-Compound a | 46.7 |
| C3: PEG-AAN-PABC-Compound a | 51.4 |
| C4: Glucose-AAN-PABC-Compound a | 46.7 |
| C5: Lacto-AAN-PABC-Paclitaxel | 59.3 |
| S3: Lacto-AAN-PABC-Adriamycin | 82.6 |
| S1: Lacto-AAN-PABC-Compound a | 86.7 |
| S7: Lacto-VAN-PABC-Compound a | 90.5 |
| S13: Lacto-TAN-PABC-Compound a | 98.6 |
| C6: AANL-Compound b | 1.6 (Not activated) |
| C7: AAN-PABC-Compound b | 38.4 |
| C8: PEG-AAN-PABC-Compound b | 51.4 |
| C9: Glucose-1-PEG-AAN-PABC-Compound b | 16.7 |
| S2: Lacto-AAN-PABC-Compound b | 88.4 |
| S8: Lacto-VAN-PABC-Compound b | 93.7 |
| S14: Lacto-VAN-PABC-Compound b | 99.5 |
| C10: Lacto-LAN-PABC-Compound b | 2.7 |
| C11: EMC-AANL-Adriamycin | 54.5 |

The above results indicate that the asparagine endopeptidase has structural requirements for the groups at both ends of the substrate peptide and the substrate peptide, and the drug and different linker linkages have different effects on drug activation: C1, C6 are not activated. The AANL linker is ineffective for compound a and compound b activation. The activation efficiencies of C2, C3, C4, C7, C8, and C9 are much lower than those of S1 and S2, indicating that Lacto has a special structure-activity relationship compared with LAC and Succinyl, which promotes the activation of the overall compound. S1 has a higher activation efficiency than C5, indicating that compound a and compound b are more suitable for Lacto-AAN-PABC-linkers than paclitaxel. The activation efficiencies of S1, S7 and S13 increased in turn, while other amino acid substitutions such as C10 did not activate, indicating that the amino acid screening optimized linker has an important role in optimizing the overall drug activation. The activation efficiency of S3 is higher than that of C11, indicating that the linker of the present invention can improve the activation efficiency of the drug.

Example 10: Effect of Compounds on Key Data (Solid Stability) in the Evaluation of Drug Properties The test was carried out by leaving it at 60° C. for 10 days in the dark. The ratio of the change in the content of the compound to the compound at time 0 was measured by HPLC, and the stability value (%) was calculated. The results are shown in Table 4 below.

TABLE 4

| Compound | Stability(%) |
|---|---|
| C1:AANL-Compound a | 96.8, stable |
| C2:AAN-PABC-Compound a | 89.4, unstable |
| C3:PEG-AAN-PABC-Compound a | 87.2, unstable |
| C4:glucose-AAN-PABC-Compound a | 85.7, unstable |
| C5:Lacto-AAN-PABC-Paclitaxel | 89.3, unstable |
| S3:Lacto-AAN-PABC-Adriamycin | 99.8, stable |
| S1:Lacto-AAN-PABC-Compound a | 96.7, stable |
| S7:Lacto-VAN-PABC-Compound a | 97.2, stable |
| S13:Lacto-TAN-PABC-Compound a | 98.6, stable |
| C6:AANL-Compound b | 91.6, stable |
| C7:AAN-PABC-Compound b | 85.6, unstable |
| C8:PEG-AAN-PABC-Compound b | 86.5, unstable |
| C9:glucose-AAN-PABC-Compound b | 90.7, stable |
| S2:Lacto-AAN-PABC-Compound b | 99.6, stable |
| S8:Lacto-VAN-PABC-Compound b | 98.4, stable |
| S14:Lacto-VAN-PABC-Compound b | 97.8, stable |
| C10:Lacto-LAN-PABC-Compound b | 92.2, stable |
| C11:EMC-AANL-Adriamycin | 96.5, stable |

The above results indicate that the present disclosure greatly enhances the stability of the drug by attaching the drug molecule to the linker of the present disclosure.

Figure 4:
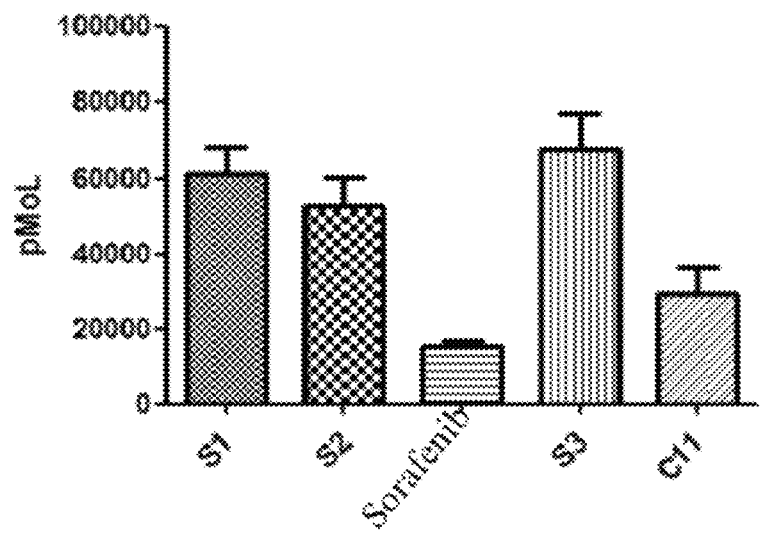
FIG. 4: Site-directed targeting of molecules leads to highly active and highly efficient molecular compounds S1, S2, S3, and C11 are distributed relative to the tumor tissue of sorafenib.

Example 11: Metabolic Distribution of the Compounds Herein Relative to Sorafenib and Other Linkers of Drugs Intravenous injection of 10 micromoles per kilogram of the drug into tumor-bearing mice, surgically obtained tumor tissue homogenate, and the drug content was determined by the HPLC method. As a result, as shown in FIG. 4, it was confirmed that the compounds S1 and S2 were multiplied in the distribution of sorafenib in the tumor, and the compound S3 also had a property of increasing the distribution in the tumor compared to C11.

Example 12: Toxicology of the Compounds Herein Relative to Sorafenib and Other Linkers Test purpose: to investigate the acute toxicity of highly activated compounds by targeted site molecules of the invention by measuring the MTD (maximum tolerated dose) experiment in mice.
Test drugs: The test drugs are shown in Table 3 below. The injections of each drug and the control drug were uniformly dissolved using water for injection, and diluted to the corresponding dose with physiological saline during the test.
Animals: the first class BALB/C mouse (purchased from Shanghai SLAC Laboratory Animal Co., Ltd.), weighing 19-21 g and all mice being female.
Methods and results: Thirty-six BALB/C mice, weighing 19-21 g, were randomly divided into 10 groups, with 10 mice in each group. As shown in Table 3, the different doses of the drug in Table 3 were dissolved in physiological saline, intravenously, and the dose at the time of death and the maximum tolerated dose (MTD) were recorded. A control test of the saline group and the adriamycin group injection (commercially available, Beijing Yue kang) was carried out, and the injection volume of each mouse was 0.2 ml. Animals were observed for 17 continuous days for presence or absence of the following behaviors on each day: piloerection, hair tousle and lackluster, lethargy, stoop and irritable reaction, and body weight and death were recorded. On the D3, D5, and D14, blood samples were taken for whole blood count. On the 14th day, the animals were dissected and observed by HE staining of heart, liver, kidney, lung, spleen and pancreas. The death rate results as shown in Table 5.

TABLE 5

The death rate results of different doses of S1, S2, S3, S4, S5 and S6 injections and saline and doxorubicin injections in the test mice

| Group | Death dose (mg/kg) | MTD (mg/kg) | Number of deaths |
|---|---|---|---|
| physiological saline | Equal volume | | 0 |
| S1 | 350 | 300 | 1 |
| S2 | 350 | 300 | 2 |
| S3 | 110 | 100 | 1 |
| S4 | 300 | 280 | 2 |
| S5 | 320 | 310 | 2 |
| S6 | 290 | 280 | 1 |
| S7 | 345 | 300 | 1 |
| S8 | 340 | 280 | 2 |
| S9 | 120 | 100 | 2 |
| S10 | 320 | 310 | 1 |
| S11 | 330 | 300 | 2 |
| S12 | 300 | 290 | 1 |
| S13 | 360 | 320 | 2 |
| S14 | 350 | 310 | 1 |
| S15 | 100 | 90 | 1 |
| S16 | 300 | 290 | 2 |
| S17 | 310 | 290 | 1 |
| S18 | 290 | 280 | 2 |
| Adriamycin | 10 | 8 | 3 |
| Sorafenib | 12 | 11 | 0 |
| C1: AANL-compound a | 80 | 65 | 1 |
| C2:AAN-PABC-compound a | 70 | 60 | 2 |
| C3: PEG-AAN-PABC-compound a | 80 | 60 | 1 |
| C4: glucose-AAN-PABC-compound a | 90 | 80 | 2 |
| C11: EMC-AANL-Adriamycin | 120 | 110 | 2 |

Figure 5:
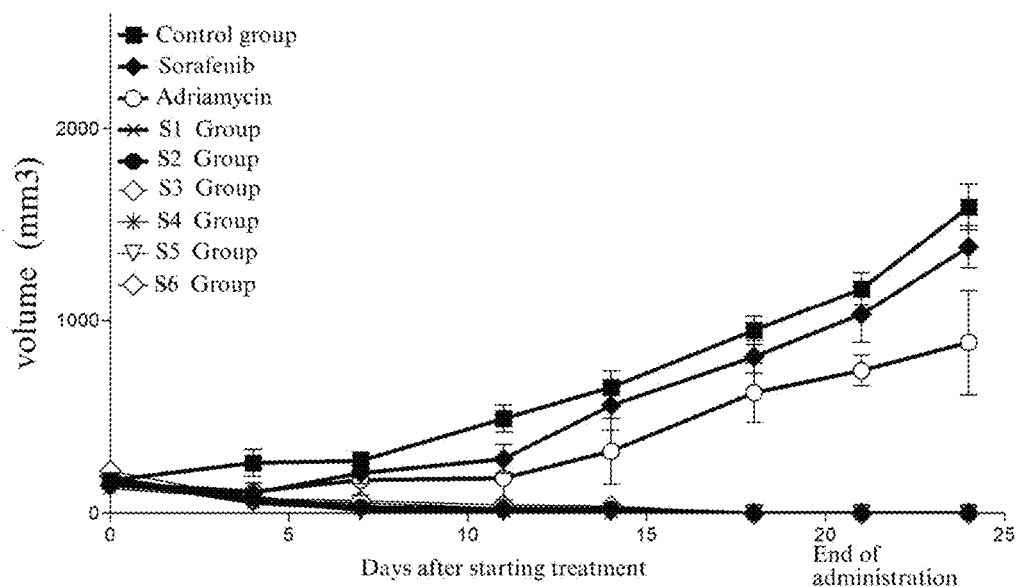
FIG. 5: Tumor size changes in site-directed targeting of molecules leads to highly active and highly efficient molecular compounds S1, S2, S3, S4, S5, S6, sorafenib and doxorubicin in tumor treatment.

Example 13: Efficacy of the Compounds Herein Relative to Sorafenib and Other Linkers In the human liver cancer HepG2 xenograft model, equimolar (30 umol/kg) of each drug (S1-S6, adriamycin and sorafenib, the control group was given normal saline), and the tumor volume after administration was tested at different time points. size. As a result, as shown in FIG. 5, the therapeutic efficacy of the compound S1-S6 administration group to the tumor was greatly improved as compared with the positive control drugs (doxorubicin and sorafenib). This is related to the targeting mechanism in the drug design concept, and the dual-targeted local release of the drug in the tumor microenvironment, so the treatment ability for the tumor is far superior to the positive control drug. At the same time, S1-S6 localized release in the tumor, rapidly reducing the tumor volume of the tumor-bearing mice, and after the administration twice, the tumor disappeared. With the increase in the number of administrations, the tumor-bearing mice of the S1-S6 administration group were cured, and after the drug was stopped, there was no tumor re-growth.

Example 14: Immunotherapy of a Compound of the Present Invention Relative to a Control Group Such as Sorafenib (1) D121 lung cancer cells purchased from ATCC were cultured in DMEM medium containing 10% fetal bovine serum at 37° C. and 5% $CO_2$, and the cells were digested with EDTA trypsin according to routine use, and passed two to three times a week for placement.

(2) Animals: C57 BALB/C mice, 6-8 weeks old, female, weighing about 18-22 g, purchased from Shanghai SLAC Laboratory Animal Co., Ltd.

3) Immunization: Mice were intraperitoneally injected with 100 μL of $5×10^5$ D121 lung cancer cells that died by repeated freeze-thaw cycles, and immunized 3 times with an interval of 2 weeks.

4) Cell seeding: Collect the tumor cells in logarithmic growth phase, adjust the D121 cell concentration to $(1×10^7/ml)$ with DMEM basal medium, 0.1 ml of the cell suspension was inoculated to the right side of each mouse subcutaneously with a 1 ml syringe. Under the skin. Tumor volume was observed and measured, and the average tumor volume reached 100-200 mm³ about 7 days after inoculation, that is, tumor cell-bearing mice were grouped and administered. The immunized group in Table 9 was immunized with D121 lung cancer cells, and the D121 dead tumor cell immunized group was injected with physiological saline as a control.

(5) Treatment procedure: i.v., S1~S8 use ⅙ MTD dose once a week for 4 weeks. The immunosuppressive regulatory point protein Anti-PD-L1 antibody was injected twice a week. A total of two weeks.

6) Experimental observation: During the whole experiment, the use and observation of experimental animals were carried out in accordance with the regulations of AAALAC. The experimental animals were observed daily after inoculation of tumor cells, and their onset and death were recorded. During the routine experiment, all experimental animals were monitored and recorded for behavior, feeding, water intake, weight change, hair shine and other abnormalities.

(7) Analysis of tumor CD8+ T cells (T lymphocyte subsets). Tumor tissues were ground and single cancer cells were isolated by filtration using 40 μm Nylon cell strainer, lysed twice with blood cell lysis buffer for 20 min, washed twice with 1% BSA-PBS buffer, centrifuged, and resuspended, and then the cells were counted again. $1×10^5$ cells were incubated with leukocyte co-antigen CD45-PE and CD8-FITC-labeled antibody for 1 hour at room temperature in the dark, and then analyzed the proportion of T lymphocyte antigen (CD8) in leukocyte common antigen (CD45)-positive cells by flow cytometry.

(8) Grouping and result measurement are shown in Table 6 below.

TABLE 6

| Group | Tumor inhibition rate/% (week 7) | CD8: CD45 (%) | Group | Tumor inhibition rate/% (week 7) | CD8: CD45 (%) |
|---|---|---|---|---|---|
| Solvent control | | 6.2 | Anti-Pd L1 Antibody | 15.5% | 15.1 |
| S1 | 53.4 | 11.0 | S1 + Anti-Pd L1 Antibody | 100% | 18.5 |
| S2 | 52.4 | 10.5 | S2 + Anti-Pd L1 Antibody | 100% | 19.1 |
| S3 | 62.5 | 14.6 | S3 + Anti-Pd L1 Antibody | 100% | 19.5 |
| S4 | 70.7 | 15.8 | S4 + Anti-Pd L1 Antibody | 100% | 20.1 |
| S5 | 76.7 | 15.3 | S5 + Anti-Pd L1 Antibody | 100% | 19.2 |
| S6 | 73.4 | 14.4 | S6 + Anti-Pd L1 Antibody | 100% | 20.3 |
| Adriamycin | 14.6 | 5.4 | DOX + Anti-Pd L1 Antibody | 27.4% | 9.6 |
| Sorafenib | 24.5 | 6.4 | Sorafenib + Anti-Pd L1 Antibody | 41.4% | 8.9 |
| C2: AAN-PABC-compound a | 25.7 | 8.6 | C2: AAN-PABC-compound a | 29.7 | 7.3 |
| C3: PEG-AAN-PABC-compound a | 20.9 | 9.3 | C3: PEG-AAN-PABC-compound a + Anti-Pd L1 Antibody | 50.6 | 10.8 |
| C4: glucose-AAN-PABC-compound a | 40.8 | 10.7 | C4: glucose-AAN-PABC-compound a + Anti-Pd L1 Antibody | 64.4 | 11.8 |

(9) Results and discussion: According to the data of Table 9, the S1-S6 compound showed good antitumor effect compared with the solvent control group and the positive control group. Moreover, by combination with Anti-Pd L1 antibody, it showed 100% anti-tumor effect, which was superior to the monotherapy group and showed very good synergistic effect. Moreover, combination therapy has a good immune promoting effect. Flow cytometry analysis showed that the proportion of CD8+ T cells in the combination treatment group increased, resulting in an increase in the number of CD8+CD45+ cells. While the control group did not change the effect of immunotherapy, non-targeted doxorubicin and sorafenib inhibited T cells.

Example 15: New Advances in the Compounds of this Study Relative to Sorafenib in the CT26 Immunotherapy Model 1) CT26 tumor cells were purchased from ATCC, and the cells were cultured using a 10% fetal bovine serum DMEM medium at 37° C., 5% $CO_2$. The cells were passaged every 3 days and the cells were used within 15 generations. Animals: C57 mice, 6-8 weeks old, all female, purchased from Shanghai SLAC Laboratory Animal Co., Ltd.

2) Tumor production: $10^6$ live CT26 tumor cells were injected subcutaneously into the back of tumor-immunized C57 mice, and treatment was started when the tumor grew to about 0.3-0.4 cm. The tumor size (mm³) of the mice was recorded and compared with the solvent control group. The tumor inhibition rate on day 42 was calculated in the solvent control group.

3) Treatment process: IV injection is used, and the drug is used at a dose of ⅓ MTD once a week Immunosuppressive IV injection treatment once a week for a total of 6 weeks of treatment.

4) The cure rate of 10 in each group was counted. After 50 days, the cured mice and wild groups were inoculated 2*105 to detect recurrence.

5) Grouping and result measurement are shown in Table 7 below.

TABLE 7

| Group | Tumor inhibition rate % (Day 42) | Number of cures | Cure rate % | Recurrence rate % (Week 7) |
|---|---|---|---|---|
| Solvent control | 0 | | 0 | — |
| Wild group | — | | — | 100 |
| S1 | 94.7 | 4 | 40 | 0 |
| S2 | 92.4 | 5 | 50 | 0 |
| S3 | 82.5 | 8 | 80 | 0 |
| S7 | 84.7 | 7 | 70 | 0 |
| S13 | 79.7 | 8 | 80 | 0 |
| S8 | 73.4% | 7 | 70% | 0 |
| S14 | 85.% | 8 | 80% | 0 |
| C11: EMC-AANL-Adriamycin | 79.5 | 4 | 40 | 25% |
| Adriamycin | 24.5% | 0 | 0 | |
| C3: PEG-AAN-PABC-Compound a | 45.6 | 0 | 0 | |
| C4: glucose-AAN-PABC-Compound a | 36.6 | 0 | 0 | |

6) Results and discussion: Compared with the control groups, the S1, S2, S3, S7, S13, S8, and S14 groups all showed a higher cure rate, that is, the tumor treatment completely disappeared. Then, CT26 tumor cells were inoculated, and the wild group was able to relapse and grow tumors. In the S1, S2, S3, S7, S13, S8, and S14 cure groups, the tumors no longer relapsed, indicating that the mice had developed immunity against tumor cells through drug treatment. The cure rate of S1, S7, and S13 is improved, indicating that the amino acid screening optimized linker has an important role in optimizing the overall efficacy.

Figure 6:
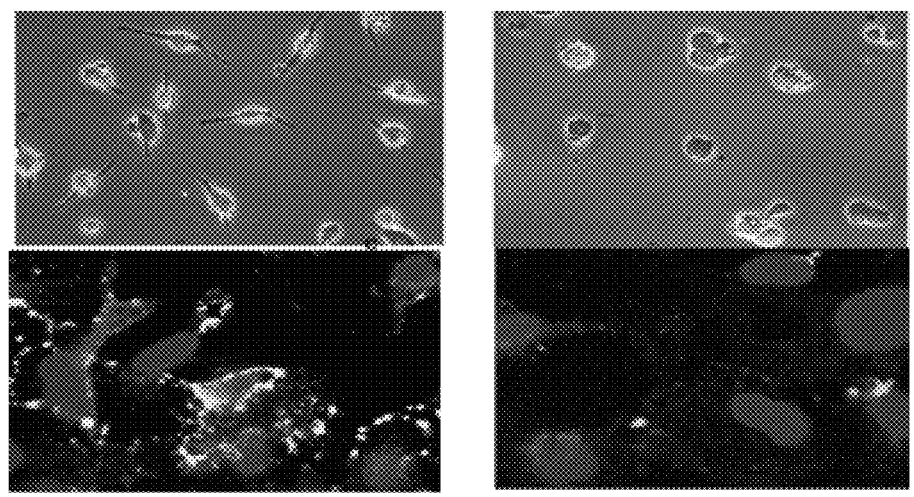
FIG. 6: The cell-differentiated bone marrow cells are M1 and M2 type macrophages, and the asparagine endopeptidase is highly expressed and secreted on the M2 type. The left panel shows tumor-induced M2 macrophages, and the right panel shows M1-inflammatory macrophages. The bright spot (green fluorescence) is the staining of the asparagine endopeptidase.

Example 16: Mechanism of Structure-Activity Relationship of the Compounds of the Present Invention to Stimulate Immunity Tumor-associated macrophages (M2 type) are an accomplice to tumor growth and recurrence. Inflammatory macrophages (M1 type) and tumor-associated macrophages (M2 type) were induced, and tumor-associated macrophages (M2 type) were highly expressed by fluorescent staining to express asparagine endopeptidase (FIG. 6).

Figure 7:
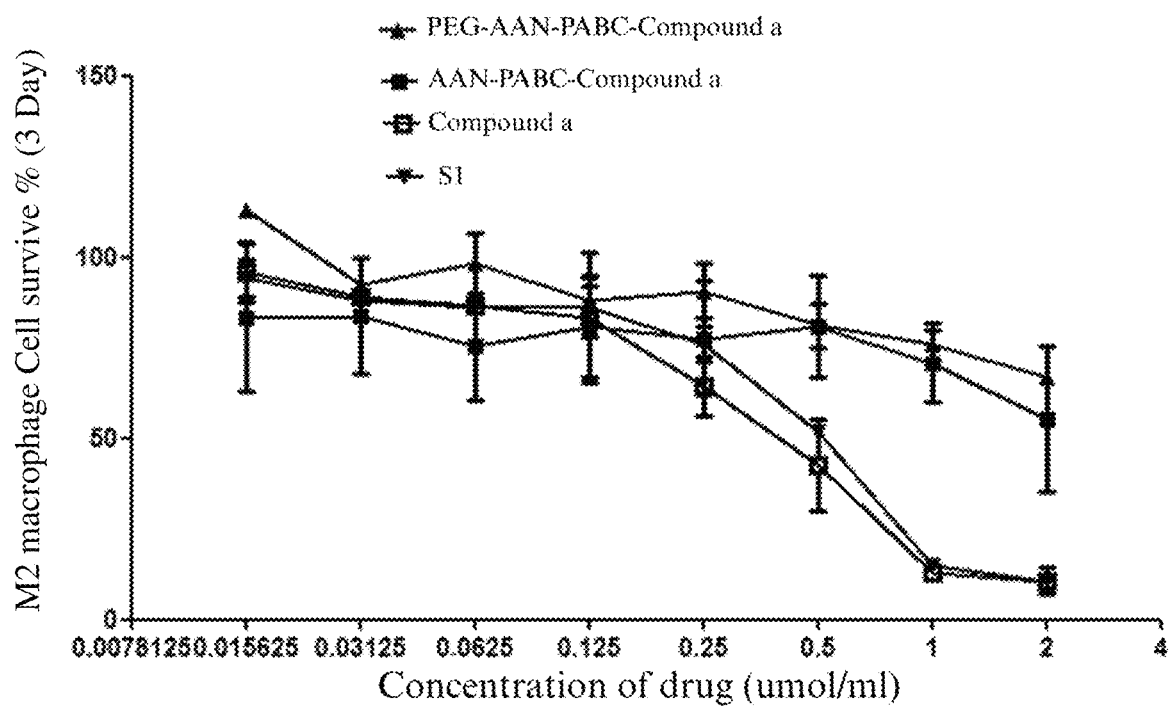
FIG. 7: Comparison of the toxicity of drugs on M2 tumor-associated macrophages.

Tumor-associated macrophages (M2 type) induced by mononuclear bone marrow cells were collected by M-CSF (10 ng/ml), the cell suspension concentration was adjusted, 140 ul per well was added, and the cells were adjusted to a density of ~3000 per plate. 5% $CO_2$, incubate at 37° C. overnight, until the cell monolayer is covered with the bottom of the well (96-well flat bottom plate), and then add a continuous concentration gradient to give different concentrations of the drug, the drug is set to 9 concentration gradients, 10 µl per well, set Three replicate wells; 5% $CO_2$, incubated at 37° C., pH 6.5 for 48 hours, observed under an inverted microscope; 20 µl of MTT solution (5 mg/ml, i.e., 0.5% MTT) was added to each well and culture was continued for 4 h. The culture was terminated, and the culture solution in the well was carefully aspirated; 100 ul of dimethyl sulfoxide was added to each well, and shaken on a shaker at a low speed for 10 min to dissolve the crystals sufficiently. The absorbance of each well was measured at an enzyme-linked immunosorbent detector at OD490 nm. At the same time, zero adjustment holes (medium, MTT, dimethyl sulfoxide), control group (cell, same concentration of drug dissolution medium, medium, MTT, dimethyl sulfoxide) were set. The toxicity of the compound to tumor-associated macrophages (M2 type) was analyzed after the test. The inhibition of tumor-associated macrophages (M2 type) by different drugs was compared. The results are shown in FIG. 7. FIG. 7 shows that the lactose-containing drug (S1) is more susceptible to phagocytosis and activation by macrophages than other methods of linker. Compound a, sorafenib, is also toxic because it is not a targeted activating drug.

Thus, molecular site-targeted results in a highly activated and highly efficient linker with a specific role in promoting tumor-associated macrophage (M2 type) phagocytosis and activating drugs, thereby inhibiting tumor-associated macrophages (M2 type).

Example 17: Pharmacodynamics and Immunotherapy of Compounds S4-S6, S9-S12 and S15-S18 in a CT26 Treatment Model The CT26 immunotherapy model was constructed as in Example 15, and the pharmacodynamic and immunotherapeutic effects of the compounds S4-S6, S9-S12 and S15-S18 in the CT26 treatment model were tested. The results are shown in Table 8 below.

TABLE 8

| Group | Tumor inhibition rate/% (at week 7) | CD8: CD45 (%) | Number of animals cured | Recurrence rate/% (at week 10) |
|---|---|---|---|---|
| Solvent control | 0 | 6.2 | 0 | 100 |
| S4 | 58.9 | 11.9 | 2 | 0 |
| S5 | 60.1 | 11.5 | 1 | 0 |
| S6 | 66.7 | 14.9 | 1 | 0 |
| S9 | 66.7 | 13.8 | 3 | 0 |
| S10 | 76.7 | 15.9 | 2 | 0 |
| S11 | 69.3 | 15.1 | 2 | 0 |
| S12 | 55.5 | 10.8 | 1 | 0 |
| S15 | 70.2 | 15.3 | 1 | 0 |
| S16 | 71.6 | 15.5 | 2 | 0 |
| S17 | 70.9 | 16.2 | 1 | 0 |
| S18 | 71.7 | 15.6 | 2 | 0 |
| DOX | 14.6 | 6.4 | 0 | — |
| Sorafenib | 15.7 | 7.2 | 0 | — |

Results and discussion: Tumor inhibition and immunotherapeutic properties of other compounds were examined in the CT26 treatment model. It can be seen from the data that other compounds have good antitumor effect and repression inhibition compared with the vehicle and the positive control group. In the results of flow cytometry analysis, the proportion of CD8+ T cells in the S7-S18 compound administration group also increased significantly compared with the positive control group, indicating that the molecules site targeting resulted in high activation and high efficiency, which increased the immunity of the body.

What is claimed is:

1. A compound represented by the following formula A or a pharmaceutically acceptable salt thereof:

Lacto-XAN-PABC-Z    (Formula A)

wherein,

X is alanine, proline or threonine;

A is alanine;

N is asparagine;

PABC is —NH-phenyl-CH$_2$—O—;

Z is a drug molecule selected from the group consisting of doxorubicin, darafinib, dovetinib, motesanib and a sorafenib derivative represented by the following formula B:

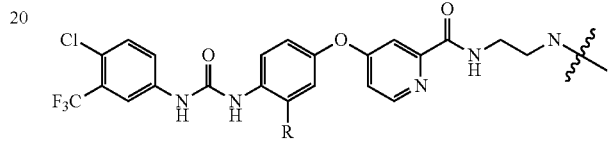

Formula B wherein R is H or halogen;

Lacto is lactobionic acid residue;

wherein the lactobionic acid residue, XAN and PABC are linked to each other by an amide bond; PABC is bonded to Z by an ester group, namely —OC(O)—.

2. The compound or a pharmaceutically acceptable salt thereof according to claim 1, wherein the compound of formula A has the structure of formula I:

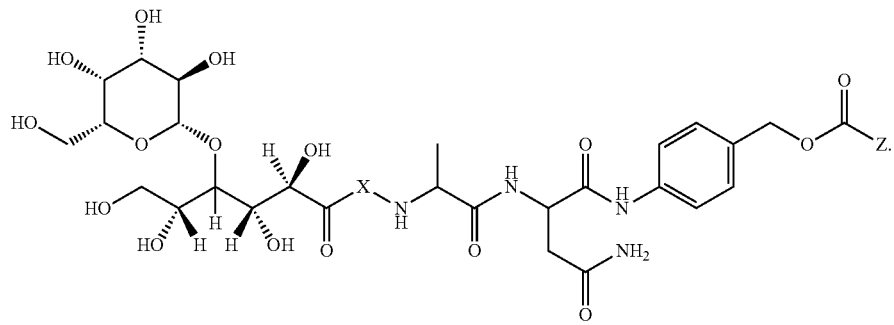

Formula I

3. The compound of claim 1 or a pharmaceutically acceptable salt thereof, wherein the compound of formula A or formula I has the structure of formula II, III or IV:

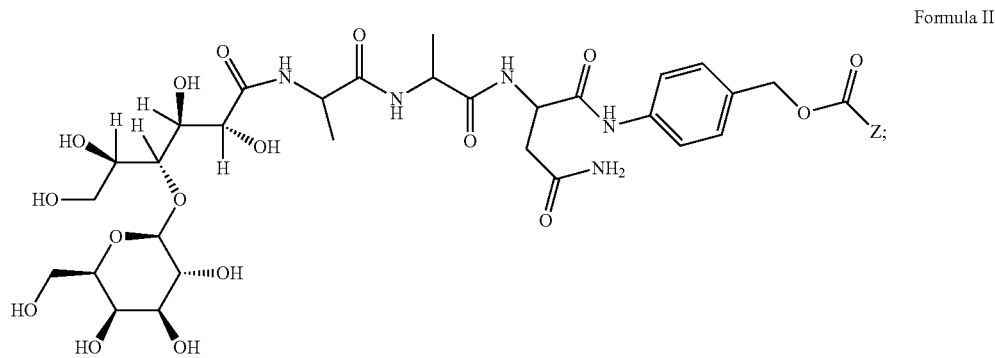

Formula II

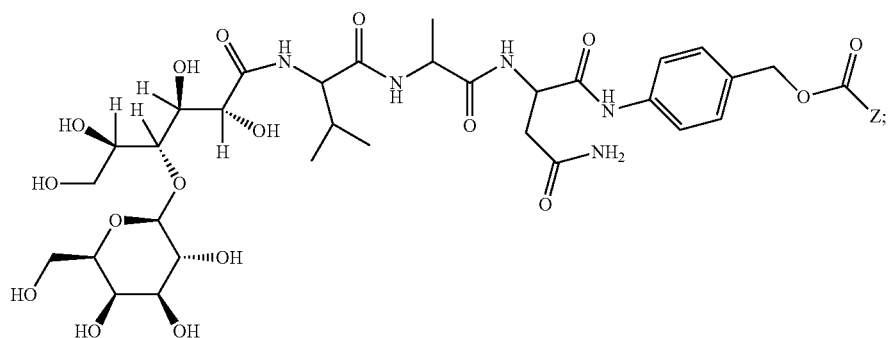
Formula III
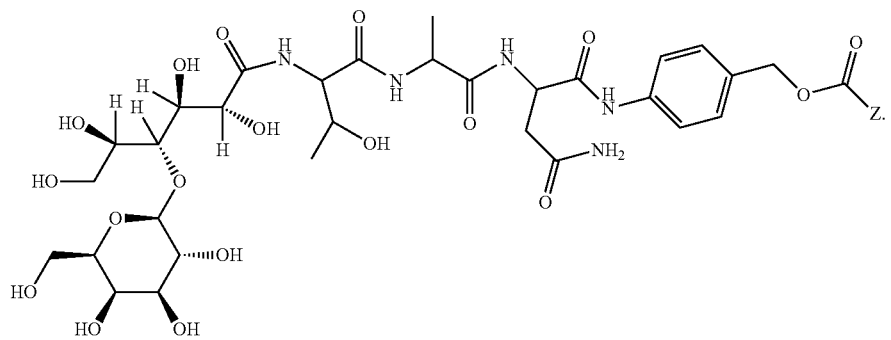
Formula IV
4. The compound or a pharmaceutically acceptable salt thereof according to claim 1, wherein the compound is selected from the group consisting of:
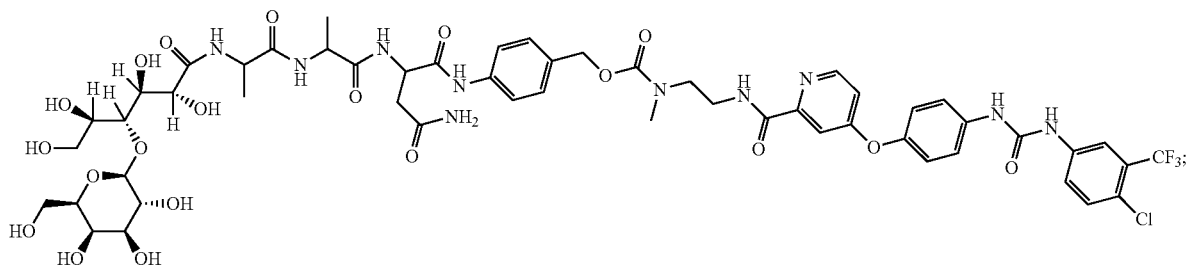
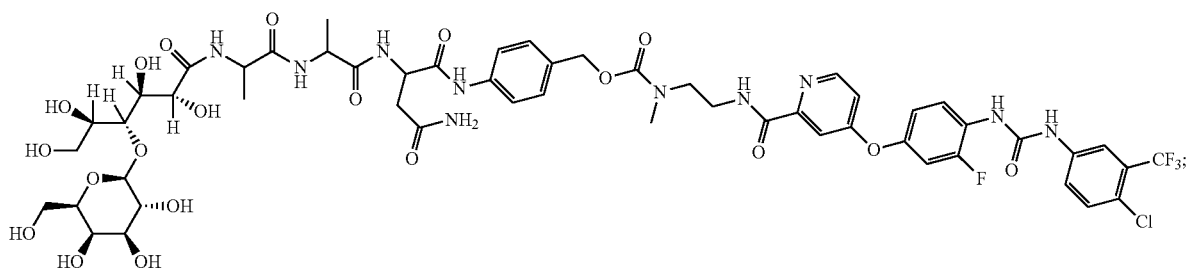

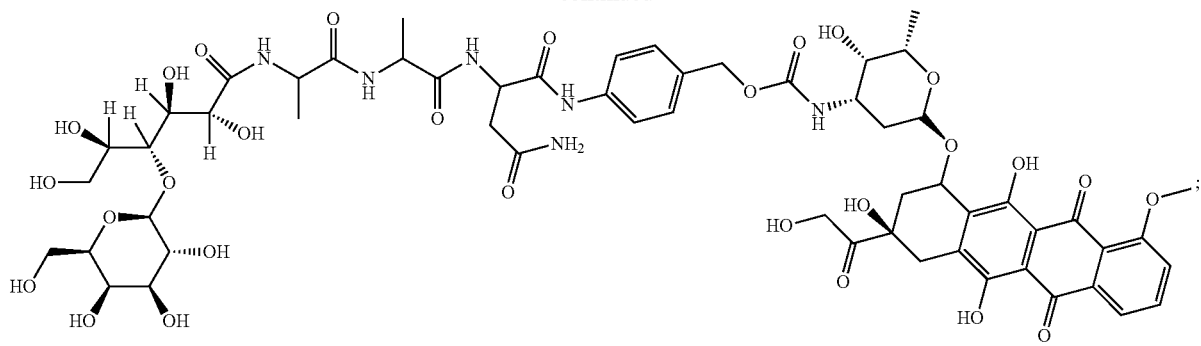
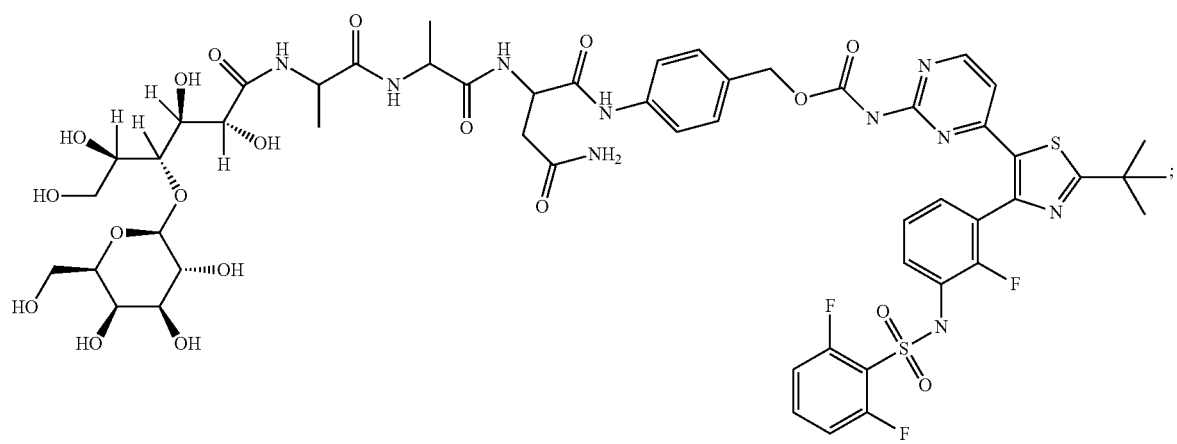
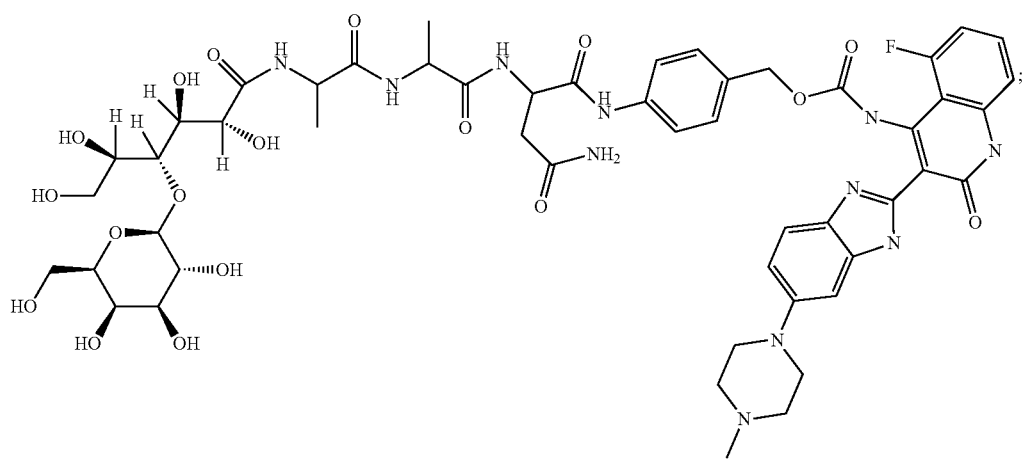
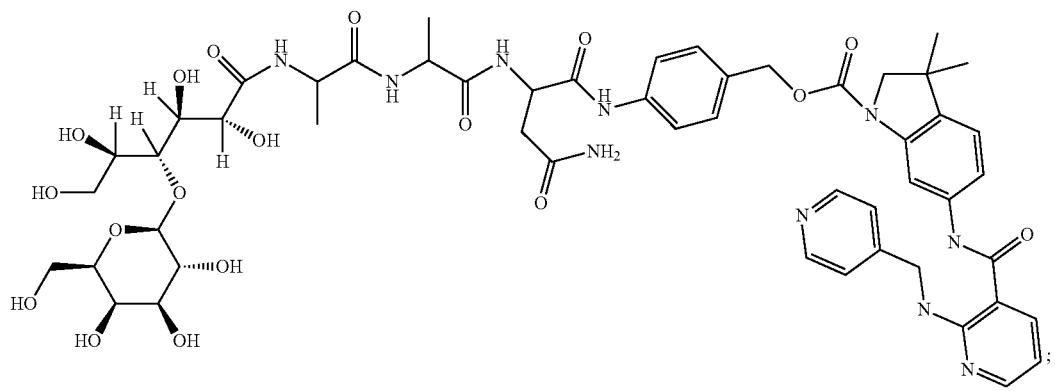

-continued
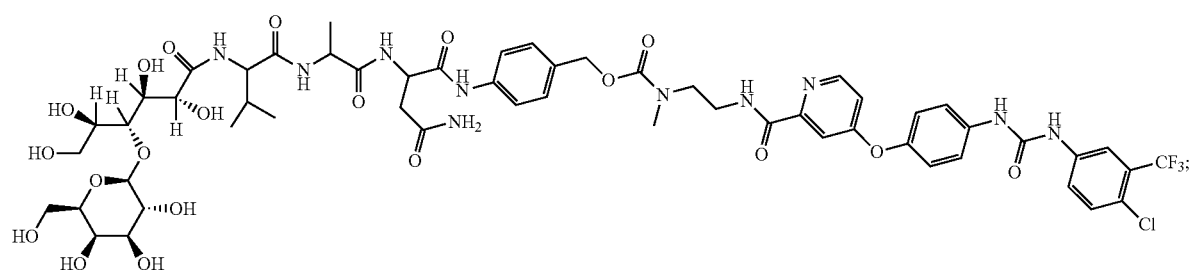
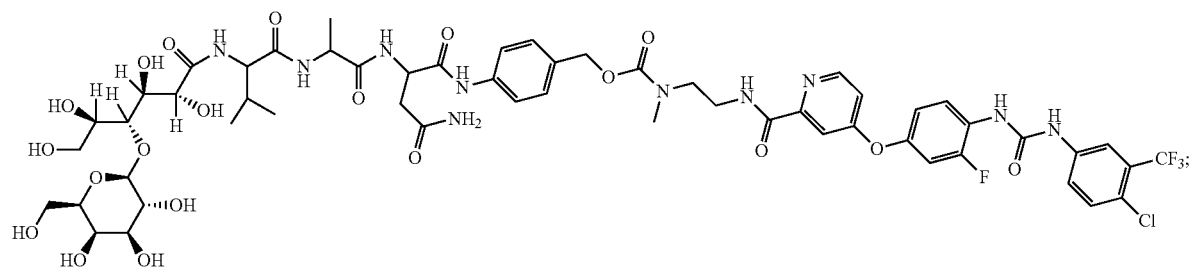
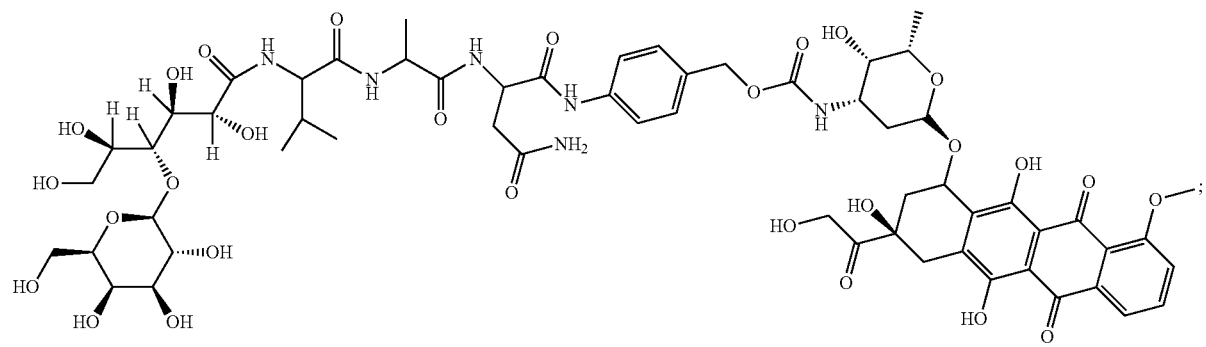
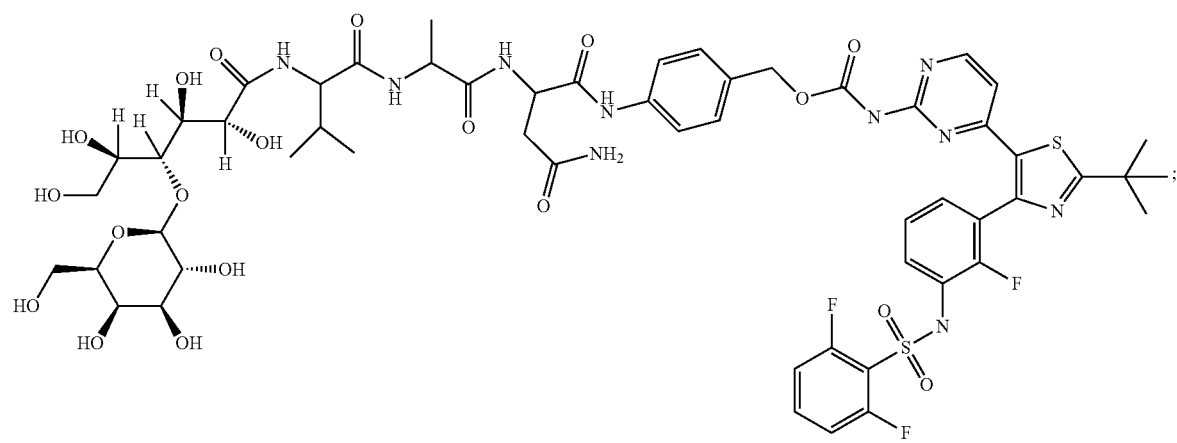

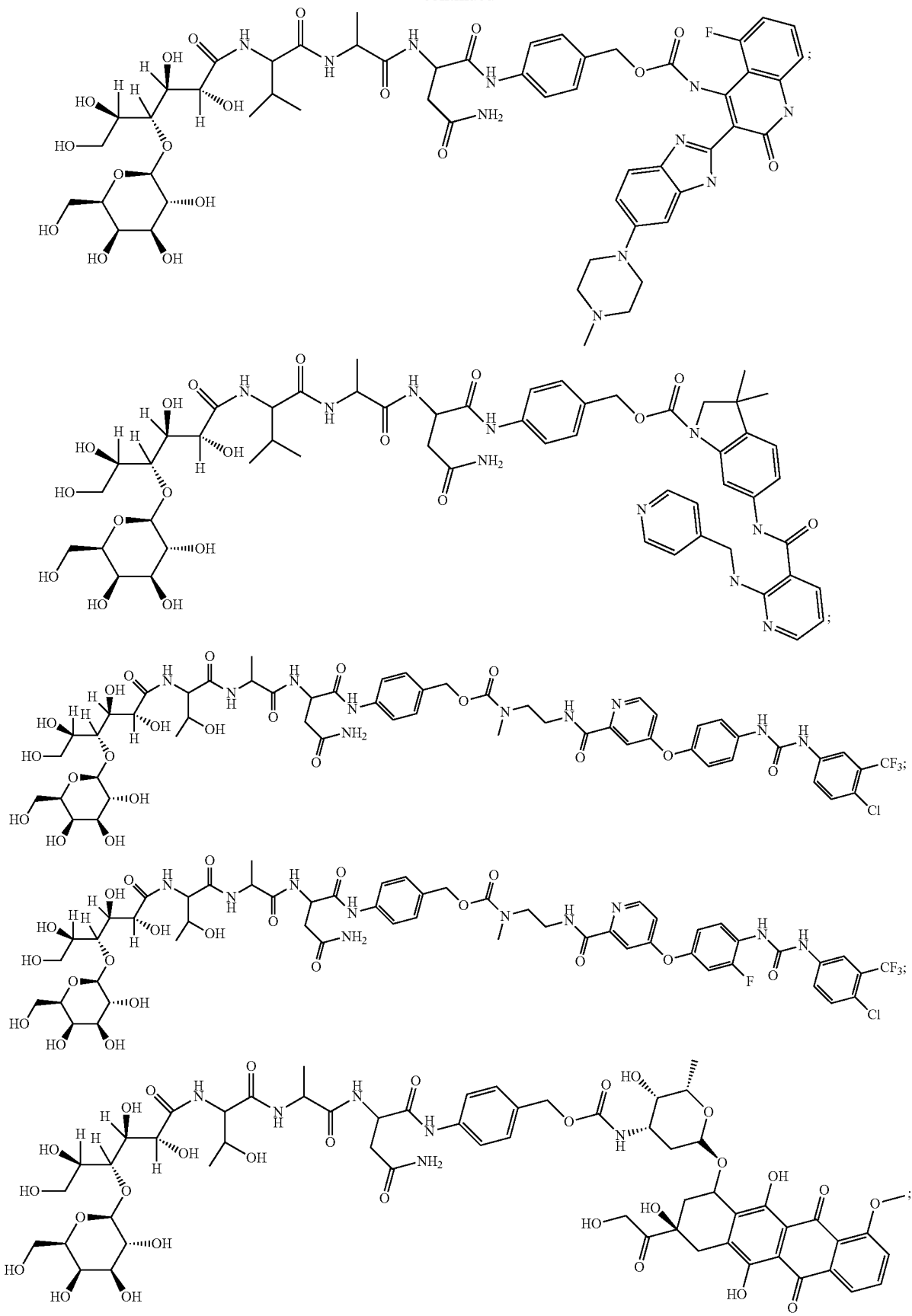

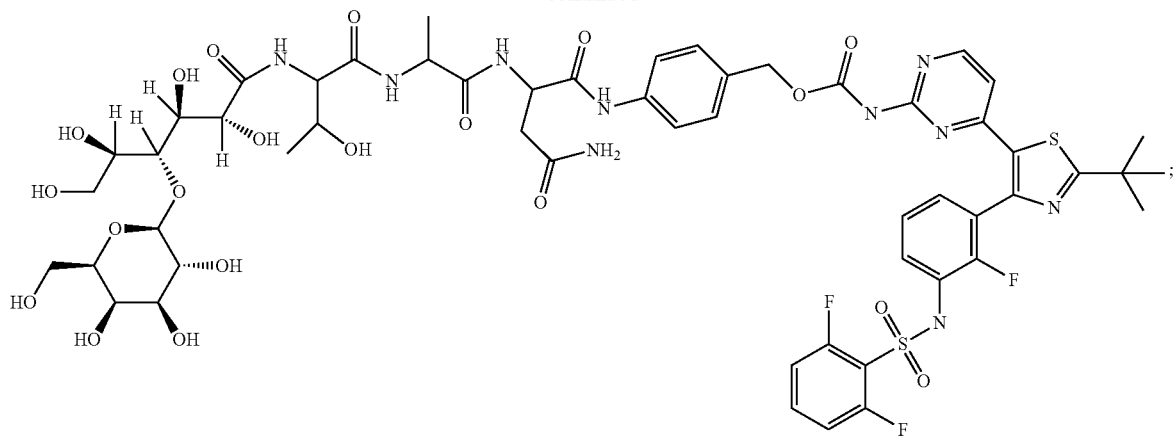
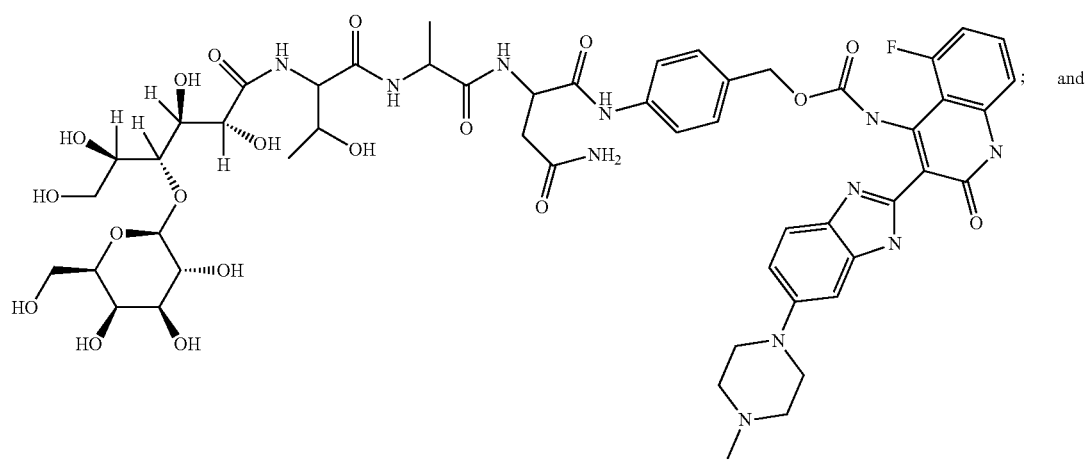
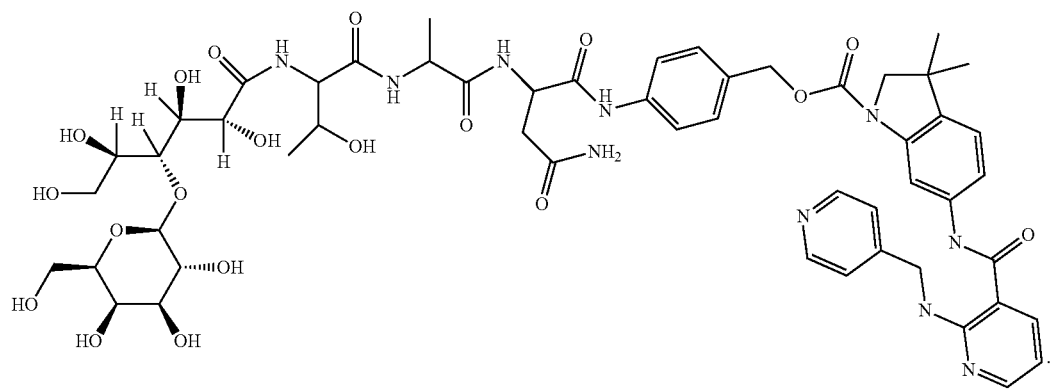

5. A pharmaceutical composition comprising the compound of claim 1, or a pharmaceutically acceptable salt thereof, and a pharmaceutically acceptable carrier.
6. The compound or a pharmaceutically acceptable salt thereof according to claim 1, wherein the compound of formula B is selected from the group consisting of compound a and compound b, namely:
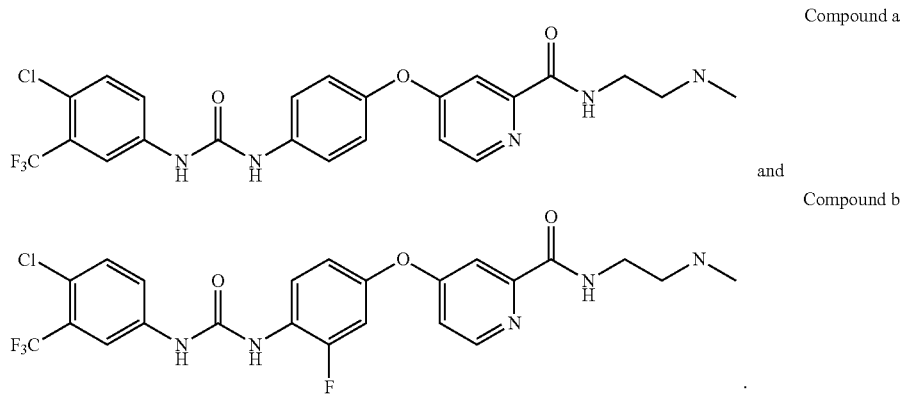
* * * * *

UNITED STATES PATENT AND TRADEMARK OFFICE
CERTIFICATE OF CORRECTION

PATENT NO. : 11,078,232 B2  
APPLICATION NO. : 16/478826  
DATED : August 3, 2021  
INVENTOR(S) : Yuan Liu Page 1 of 2

It is certified that error appears in the above-identified patent and that said Letters Patent is hereby corrected as shown below:

On the Title Page

Item [57], Line 10, after "—OC(O)—" insert --Lacto-XAN-PABC-Z (Formula A)--.

In the Specification

Column 2, Line 46, delete "darafenib, dovetinib," and insert --dabrafenib, dovitinib,--.

Columns 5-6, Line 2, delete "Darafinib" and insert --Dabrafenib--.

Columns 5-6, Line 4, delete "Dovetinib" and insert --Dovitinib--.

Columns 9-10, Line 2, delete "Darafinib" and insert --Dabrafenib--.

Columns 9-10, Line 4, delete "Dovetinib" and insert --Dovitinib--.

Columns 13-14, Line 2, delete "Darafinib" and insert --Dabrafenib--.

Columns 13-14, Line 4, delete "Dovetinib" and insert --Dovitinib--.

Column 18, Line 53, delete "darafinib, dovetinib" and insert --dabrafenib, dovitinib--.

Column 19, Line 19, delete "darafinib," and insert --dabrafenib,--.

Column 19, Line 20, delete "dovetinib" and insert --dovitinib--.

Column 39, Line 58, delete "darafenib," and insert --dabrafenib,--.

Column 39, Line 60, delete "dovetinib," and insert --dovitinib,--.

Signed and Sealed this  
Twenty-ninth Day of March, 2022

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)  Page 2 of 2
U.S. Pat. No. 11,078,232 B2

Column 44, Line 41, delete "Glucose-1" and insert --Glucose-l--.

Column 48, Line 65, delete "week" and insert --week.--.

In the Claims

Column 51, Claim 1, Line 31, delete "darafinib, dovetinib," and insert --dabrafenib, dovitinib,--.

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Substrate peptide cleaved by enzyme

<400> SEQUENCE: 1

Ala Ala Asn Leu
1